US008846985B2

(12) United States Patent
Allgeier et al.

(10) Patent No.: US 8,846,985 B2
(45) Date of Patent: Sep. 30, 2014

(54) PRODUCTION OF ALPHA, OMEGA-DIOLS

(71) Applicant: E I du Pont de Nemours and Company, Wilmington, DE (US)

(72) Inventors: Alan Martin Allgeier, Wilmington, DE (US); Wathudura Indika Namal De Silva, Rahway, NJ (US); Carl Andrew Menning, Newark, DE (US); Joachim C Ritter, Wilmington, DE (US); Sourav Kumar Sengupta, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/870,091

(22) Filed: Apr. 25, 2013

(65) Prior Publication Data

US 2013/0289319 A1 Oct. 31, 2013

Related U.S. Application Data

(60) Provisional application No. 61/639,436, filed on Apr. 27, 2012.

(51) Int. Cl.
| | |
|---|---|
| *C07C 27/04* | (2006.01) |
| *C07C 29/132* | (2006.01) |
| *C07C 209/16* | (2006.01) |
| *C07D 309/06* | (2006.01) |
| *B01J 27/188* | (2006.01) |
| *B01J 23/888* | (2006.01) |
| *C07C 29/60* | (2006.01) |

(52) U.S. Cl.
CPC ............... *C07C 29/60* (2013.01); *B01J 27/188* (2013.01); *B01J 23/888* (2013.01); *C07C 209/16* (2013.01)
USPC ........... 568/861; 568/865; 564/479; 564/480; 549/427

(58) Field of Classification Search
USPC ................................... 568/861, 865; 549/427
See application file for complete search history.

(56) References Cited

U.S. PATENT DOCUMENTS

| | | | |
|---|---|---|---|
| 2,082,025 A | 6/1937 | Peters, Jr. | |
| 2,201,347 A | 5/1940 | Rittmeister | |
| 2,440,929 A | 5/1948 | Frederick | |
| 2,768,213 A | 10/1956 | Whetstone et al. | |
| 3,070,633 A | 12/1962 | Utne et al. | |
| 3,083,236 A | 3/1963 | Utne et al. | |
| 3,189,651 A | 6/1965 | Ellery et al. | |
| 3,215,742 A | 11/1965 | Horlenko et al. | |
| 3,223,714 A | 12/1965 | Manly et al. | |
| 3,268,588 A | 8/1966 | Horlenko et al. | |
| 3,270,059 A | 8/1966 | Winderl et al. | |
| 3,917,707 A | 11/1975 | Williams et al. | |
| 3,933,930 A | 1/1976 | Dougherty et al. | |
| 4,254,059 A | 3/1981 | Grey | |
| 4,400,468 A | 8/1983 | Faber | |
| 4,401,823 A | 8/1983 | Arena | |
| 4,780,552 A | 10/1988 | Wambach et al. | |
| 5,112,994 A | 5/1992 | Koseki et al. | |
| 5,210,335 A | 5/1993 | Schuster et al. | |
| 5,412,111 A | 5/1995 | Matsumoto et al. | |
| 5,538,891 A | 7/1996 | Schneider et al. | |
| 5,696,303 A | 12/1997 | Darsow et al. | |
| 5,981,769 A | 11/1999 | Baur et al. | |
| 6,008,418 A | 12/1999 | Baur et al. | |
| 6,087,296 A | 7/2000 | Harper et al. | |
| 6,147,208 A | 11/2000 | Achhammer et al. | |
| 6,265,602 B1 | 7/2001 | Voit et al. | |
| 6,403,845 B1 | 6/2002 | Pfeffinger et al. | |
| 6,407,294 B1 | 6/2002 | Breitscheidel et al. | |
| 6,433,192 B1 | 8/2002 | Fischer et al. | |
| 6,462,220 B1 | 10/2002 | Luyken et al. | |
| 6,593,481 B1 | 7/2003 | Manzer | |
| 6,818,781 B2 | 11/2004 | Bhatia | |
| 7,019,155 B2 | 3/2006 | Manzer | |

(Continued)

FOREIGN PATENT DOCUMENTS

| | | |
|---|---|---|
| CA | 2800797 A1 | 12/2011 |
| CN | 101628875 A | 1/2010 |

(Continued)

OTHER PUBLICATIONS

Office action dated Feb. 27, 2014 for copending U.S. Appl. No. 13/870,095.
Office action dated Feb. 27, 2014 for copending U.S. Appl. No. 13/870,099.
Co-pending U.S. Appl. No. 14/031,356, filed Sep. 19, 2013.
Co-pending U.S. Appl. No. 61/782,172, filed Mar. 14, 2013.
Co-pending U.S. Appl. No. 61/782,198, filed Mar. 14, 2013.
Notice of allowance dated Jan. 13, 2014 for copending U.S. Appl. No. 13/729,494.
Abe, R. et al, "Photocatalytic overall water splitting under visible light by TaON and WO3 with an IO3-/I- shuttle redox mediator", Chem Commun, 2005, 3829-3831.

(Continued)

Primary Examiner — Brian J Davis

(57) ABSTRACT

Disclosed herein are processes for preparing an $\alpha,\omega$-$C_n$-diol, wherein n is 5 or greater, from a feedstock comprising a $C_n$ oxygenate. In one embodiment, the process comprises contacting the feedstock with hydrogen gas in the presence of a catalyst comprising a first metal component comprising Ni, Ir, Pt, Rh, Ru, Pd, Fe, Ag, or Au; a heteropoly acid component comprising $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$ $Cs_{2.5}H_{0.5}[Si(W_3O_{10})_4]$, or mixtures thereof; optionally a second metal component comprising Cr, a Cr oxide, Ni, a Ni oxide, Fe, a Fe oxide, Co, a Co oxide, Mn, a Mn oxide, Mo, a Mo oxide, W, a W oxide, Re, a Re oxide, Zn, a Zn oxide, $SiO_2$, or $Al_2O_3$; optionally at least one promoter comprising Na, K, Mg, Rb, Cs, Ca, Sr, Ba, Ce, or mixtures thereof; and optionally a support. In one embodiment, the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. The $C_n$ oxygenate may be obtained from a biorenewable resource.

15 Claims, No Drawings

(56) References Cited

U.S. PATENT DOCUMENTS

| | | | |
|---|---|---|---|
| 7,230,145 B2* | 6/2007 | Kadowaki et al. ............ 568/865 |
| 8,053,608 B2 | 11/2011 | Kouno et al. | |
| 8,053,615 B2 | 11/2011 | Cortright et al. | |
| 8,501,989 B2 | 8/2013 | Boussie et al. | |
| 8,524,925 B2 | 9/2013 | Sabesan et al. | |
| 8,669,393 B2 | 3/2014 | Boussie et al. | |
| 2003/0212298 A1 | 11/2003 | Brasse et al. | |
| 2006/0014988 A1 | 1/2006 | Fischer et al. | |
| 2007/0287845 A1 | 12/2007 | Lilga et al. | |
| 2008/0200698 A1 | 8/2008 | Reichert et al. | |
| 2009/0156841 A1 | 6/2009 | Sanborn et al. | |
| 2009/0314992 A1 | 12/2009 | Pinkos et al. | |
| 2010/0113841 A1 | 5/2010 | Suzuki et al. | |
| 2010/0216958 A1 | 8/2010 | Peters et al. | |
| 2010/0274030 A1 | 10/2010 | Bevinakatti et al. | |
| 2010/0317822 A1 | 12/2010 | Boussie et al. | |
| 2011/0040131 A1 | 2/2011 | Kouno et al. | |
| 2011/0071306 A1 | 3/2011 | Robinson | |
| 2011/0218318 A1 | 9/2011 | Boussie et al. | |
| 2011/0263916 A1 | 10/2011 | Bao et al. | |
| 2011/0312051 A1 | 12/2011 | Kalnes et al. | |
| 2012/0010419 A1 | 1/2012 | Pinkos et al. | |
| 2012/0022298 A1 | 1/2012 | Pinkos et al. | |
| 2012/0035399 A1 | 2/2012 | Abillard et al. | |
| 2012/0059174 A1 | 3/2012 | Abillard et al. | |
| 2012/0116122 A1 | 5/2012 | Feist et al. | |
| 2012/0172579 A1 | 7/2012 | Qiao et al. | |
| 2013/0172578 A1 | 7/2013 | Allgeier et al. | |
| 2013/0172586 A1 | 7/2013 | Desilva et al. | |
| 2013/0184495 A1 | 7/2013 | Dias et al. | |

FOREIGN PATENT DOCUMENTS

| | | |
|---|---|---|
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A2 | 3/2010 |
| WO | 2010033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

Adkins, H. et al, "The catalytic hydrogenation of organic compounds over copper chromite", J Am Chem Soc (1931), vol. 53, 1093.

Alexeev, O.S. et al, "gamma-Al2O3-Supported Pt catalysts with extremely high dispersions resulting from Pt-W interactions", J Catal, 190 (2000) 157-17.

Binder et al., "Simple chemical transformation of lignocellulosic biomass into furans for fuels and chemicals", J Am Chem Soc (2009) 131, 1979-1985.

Blanc, B. et al, "Starch-derived polyols for polymer technologies: preparation by hydrogenolysis on metal catalysts", Green Chemistry, Apr. 2000, 89-91.

Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.

Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.

Caes et al., "Conversion of Fructose into 5-(Hydroxymethyl)furfural in Sulfolane", ChemSusChem, (2011), 4(3), 353-356.

Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.

Chen, K. et al, "C—O bond hydrogenolysis of cyclic ethers with OH groups over rhenium-modified supported iridium catalysts", J Catalysis (2012) vol. 294, 171-183.

Chia, M. et al, "Selective hydrogenolysis of polyols and cyclic ethers over bifunctional surface sites on rhodium-rhenium catalysts", J Am Chem Soc (2011) vol. 133, No. 32, 12675-12680.

Connor, R. et al, "Hydrogenolysis of Oxygenated Organic Compounds", J Am Chem Soc (1932), vol. 54, 4678-4690.

Corma, A. "Inorganic Solid Acids and Their Use in Acid-Catalyzed Hydrocarbon Reactions", (1995) Chem. Rev., 95, 559-614.

Diebold, U. "The surface science of titanium dioxide", Surface Science Reports 48 (2003) 53-229.

Efremov, A.A., "Transformations of levoglucosenone at the anhydroglucoside bond", Chem Natural Compounds (1998) 34, 5, 582-589.

Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.

French, G.J. et al, "A re-investigation of the thermal decomposition of ammonium paratungstate", J. Mat. Sci, 16 (1981) 3427-3436.

Gong, L. et al, "Selective hydrogenolysis of glycerol to 1,3-propanediol over a Pt/WO3/TiO2/SiO2 catalyst in aqueous media", Appl Catal A General 390 (2010) 119-126.

Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.

Helberger et al, Justus Liebigs Annalen der Chemie (1949) 561, 215-220.

Huang, L. et al, "Direct conversion of glycerol into 1,3-propanediol over Cu—H4SiW12O40/SiO2 in vapor phase", Catal Lett, 131 (2009) 312-320.

Jae, J. et al, "Investigation into the shape selectivity of zeolite catalysts for biomass conversion", Journal of Catalysis (2011) 279, 257-268.

Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.

Jayaraman, S. et al, "Synthesis and Characterization of Pt-WO3 as Methanol Oxidation Catalysts for Fuel Cells", J Phys Chem B, 2005, 109, 22958-22966.

Jung, M.E. et al, "Synthesis of Methylene-Expanded 2',3'-Dideoxyribonucleosides", J Organic Chemistry 63 (1998) 8133-8144.

Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.

Karinen, R. et al, "Biorefining: heterogeneously catalyzed reactions of carbohydrates for the production of furfural and hydroxymethyfurfural", Chem Sus Chem (2011) 4, 1002-1016.

Kaufmann, W.E. et al, "The use of platinum oxide as a catalyst in the reduction of organic compounds. IV. Reduction of furfural and its derivatives", J Am Chem Soc (1923) 45, 3029-3044.

Kiss, A.B. et al, "Thermal polycondensation of ammonium paratungstate, (NH4)10[W12O40(OH)2].4H2O", J. Materials Sci, 13 (1978) 2541-2547.

Koso, S. et al, "Chemoselective hydrogenolysis of tetrahydrofurfuryl alcohol to 1,5-pentanediol", Chem. Commun. (2009) 2035-2037.

(56) References Cited

OTHER PUBLICATIONS

Koso, S. et al, "Promoting effect of Mo on the hydrogenolysis of tetrahydrofurfuryl alcohol to 1,5-pentanediol over Rh/SiO2", J Catalysis 267 (2009), 89-92.

Kuba, S. et al, "Structure and properties of tungstated zirconia catalysts for alkane conversion", J Catalysis, 216 (2003) 353-361.

Lee, U. et al, "Structure of pentasodium trihydrogenhexatungstoplatinate(IV) icosahydrate", Acta Cryst. (1983) C39, 817-819.

Li, N.; Huber, G.W., "Aqueous-phase hydrodeoxygenation of sorbitol with Pt/SiO2-Al2O3: identification of reaction intermediates", Journal of Catalysis (2010) 270, 48-59.

Li, N. et al, "Renewable gasoline from aqueous phase hydrodeoxygenation of aqueous sugar solutions prepared by hydrolysis of maple wood", Green Chemistry 2011, 13, 91-101.

Liu, L. et al, "Mesoporous WO3 supported Pt catalyst for hydrogenolysis of glycerol to 1,3-propanediol", Chin. J Catal., 2012, 33, 1257-1261.

Miftakhov, M.S. et al, "Levoglucosenone: the properties, reactions, and use in fine organic synthesis", Russian Chem Reviews (1994) 63(10) 869-882.

Nakagawa, Y. et al, "Heterogeneous catalysis of the glycerol hydrogenolysis", Catal Sci Technol 2011, 1, 179-190.

Nakagawa, Y. et al., "Production of 1,5-pentanediol from biomass via furfural and tetrahydrofurfuryl alcohol", Catalysis Today 195 (2012) 136-143.

Nikolla, E. et al., "'One-Pot' Synthesis of 5-(Hydroxymethyl)furfural from Carbohydrates Using Tin-Beta Zeolite", ACS Catal. (2011), 1, 408-410.

Okuhara, T. et al, "Insoluble heteropoly compounds as highly active catalysts for liquid-phase reactions", J. Mol. Catal. 74 (1992) 247-256.

Ott, L. et al, "Catalytic Dehydration of Glycerol in sub- and supercritical water: a new chemical process for acrolein production", Green Chemistry, 2006, pp. 214-220, vol. 8.

Pae, Y.I. et al, "Characterization of NiO—TiO2 modified with WO3 and catalytic activity for acid catalysis", Bull. Korean Chem. Soc. 2004, vol. 25(12), 1881-1888.

Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.

Roman-Leshkov, Y. et al., "Solvent effects on fructose dehydration to 5-hydroxymethylfurfural in biphasic systems saturated with inorganic salts", Top Catal (2009) 52:297-303.

Shafizadeh, F. et al., "Some Reactions of Levoglucosenone", Carbohydrate Research, 1979, pp. 169-191, vol. 71.

SRI Process Economics Program, 31, Hexamethylenediamine Nov. 1967.

Ten Dam, J. et al, "Pt/Al2O3 catalyzed 1,3-propanediol formation from glycerol using tungsten additives", ChemCatChem (2013), 5(2), 497-505.

Tong, X. et al, "Biomass into chemicals: conversion of sugars to furan derivatives by catalytic processes", Appl. Catalysis A General, 385 (2010) 1-13.

Tripathy, P.K. et al, "A comparative study on the thermal decomposition of ammonium p-tungstate in batch and fluidized-bed reactors", Ind Eng Chem Res 36 (1997) 3602-3606.

Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.

Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.

Yamazoe, S. et al, "XAFS Study of Tungsten L1-, L3-Edges: Structural Analysis of Loaded Tungsten Oxide Species", Envir Sci, Research Frontiers 2008, Spring 8, 138-139.

Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.

Yoshinaga, Y. et al, "Shape-selective oxidation catalysed by a Pt-promoted ultramicroporous heteropoly compound", J.Chem. Soc. Faraday Trans 1998, 94(15) 2235-2240.

Zanardi, M.M. et al, "Synthesis of a simple chiral auxiliary derived from levoglucosenone and its application in a Diels-Alder reaction", Tetrahedron letters 50 (2009) 999-1002.

International Search Report dated Mar. 29, 2013, PCT/US2012/062314.

International Search Report dated Apr. 29, 2013, PCT/US2012/071891.

International Search Report dated Apr. 29, 2013, PCT/US2012/071907.

International Search Report dated Apr. 29, 2013, PCT/US2012/071893.

International Search Report dated Apr. 29, 2013, PCT/US2012/071912.

International Search Report dated Apr. 30, 2013, PCT/US2012/071894.

International Search Report dated Jul. 26, 2013, PCT/US2013/038403.

International Search Report dated Jul. 18, 2013, PCT/US2013/038418.

International Search Report dated Jul. 24, 2013, PCT/US2013/038441.

International Search Report dated Jul. 24, 2013, PCT/US2013/038436.

Office actions dated Jun. 26, 2013 and Sep. 13, 2013 for copending U.S. Appl. No. 13/729,390.

Office actions dated Sep. 27, 2013 and Dec. 17, 2013 for copending U.S. Appl. No. 13/729,464.

Notice of allowance dated Oct. 1, 2013 for copending U.S. Appl. No. 13/729,494.

Notice of allowance dated Nov. 19, 2013 for copending U.S. Appl. No. 13/729,401.

Office action dated Dec. 20, 2013 for copending U.S. Appl. No. 13/729,507.

notice of allowance dated Apr. 28, 2014 for copending U.S. Appl. No. 13/729,494.

notice of allowance dated Apr. 29, 2014 for copending U.S. Appl. No. 13/729,507.

office action dated May 7, 2014 for copending U.S. Appl. No. 13/729,390.

Database CAPLUS on STN, AN 1979:151575, Nishino et al, JP 53149905 A, Dec. 27, 1978 (abstract).

Database WPIX on STN, AN 1979-11181B [197906], Nishino et al, JP53149905 A Dec. 27, 1978 (abstract).

* cited by examiner

PRODUCTION OF ALPHA, OMEGA-DIOLS

This application claims priority under 35 U.S.C. §119(e) from, and claims the benefit of, U.S. Provisional Application No. 61/639,436 filed Apr. 27, 2012, which is by this reference incorporated in their entirety as a part hereof for all purposes.

FIELD OF DISCLOSURE

The present invention relates to processes for preparing alpha, omega-diols ("α,ω-diols"). More particularly, the present invention relates to processes for preparing α,ω-diols by selective hydrodeoxygenation of oxygenated compounds which can be derived from carbohydrates or biologic sources.

BACKGROUND

Alpha, omega-diols such as 1,5-pentanediol and 1,6-hexanediol are useful as chemical intermediates for the production of, e.g., agrichemicals, pharmaceuticals, and polymers. For example, α,ω-diols can be used as plasticizers and as comonomers in polyesters and polyether-urethanes. It has become increasingly desirable to obtain industrial chemicals such as α,ω-diols, or their precursors, from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon 66. 1,6-Hexanediol can be converted by known methods to 1,6-hexamethylene diamine, a starting component in nylon production. 1,6-Hexanediol is typically prepared from the hydrogenation of adipic acid or its esters or the hydrogenation of caprolactone or its oligomers. For example, in WO 2011/149339, deVries J-G, et al describe a process for the preparation of caprolactone, caprolactam, 2,5-tetrahydrofuran-dimethanol, 1,6-hexanediol or 1,2,6-hexanetriol from 5-hydroxymethyl-2-furfuraldehyde and teach that 1,2,6-hexanetriol may be hydrogenated to 1,6-hexanediol using a catalyst based on palladium, nickel, rhodium, ruthenium, copper and chromium or mixtures thereof. Further, the catalysts may be doped with one or more other elements, such as rhenium.

JP 2003-183200 teaches a method for preparation of 2,5-diethyl-1,6-hexanediol from tetrahydropyran derivatives, e.g. 2,5-diethyltetrahydropyran-2-methanol, comprising hydrogenation of the starting material in the presence of a metal catalyst carried on an acidic support, notably 5% $Pt/Al_2O_3$ and 5% $Pt/SiO_2$—$Al_2O_3$ at 200-240° C. Yields ranged from 40 to 61%.

There is an existing need for processes to make α,ω-diols, especially $C_5$ and $C_6$ α,ω-diols, and synthetic intermediates useful in the production of α,ω-diols, from renewable biosources. There is an existing need for processes to produce 1,5-pentanediol, 1,6-hexanediol, and other α,ω-diols at high yield and high selectivity from biomass-derived starting materials, including 1,2,6-hexanetriol, tetrahydrofuran-2,5-dimethanol, and 2-hydroxymethyltetrahydropyran.

SUMMARY

In one embodiment, a process is provided for preparing an α,ω-$C_n$-diol is provided, the process comprising the steps:

(a) providing a feedstock comprising a $C_n$ oxygenate;

(b) contacting the feedstock with hydrogen gas, in the presence of a catalyst and at a temperature and for a time sufficient to form a product mixture comprising an α,ω-$C_n$-diol;

wherein n is 5 or greater; and wherein the catalyst comprises a first metal component, a heteropoly acid component, optionally a second metal component, optionally at least one promoter, and optionally a support; wherein:

the first metal component comprises Ni, Ir, Pt, Rh, Ru, Pd, Fe, Ag, or Au;

the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof;

the second metal component comprises Cr, a Cr oxide, Ni, a Ni oxide, Fe, a Fe oxide, Co, a Co oxide, Mn, a Mn oxide, Mo, a Mo oxide, W, a W oxide, Re, a Re oxide, Zn, a Zn oxide, $SiO_2$, or $Al_2O_3$; and the promoter comprises Na, K, Mg, Rb, Cs, Ca, Sr, Ba, Ce, or mixtures thereof.

In one embodiment, the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In one embodiment, the support comprises $SiO_2$, $TiO_2$, zeolites, or mixtures thereof.

In one embodiment, the $C_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural with ketones and/or aldehydes; and condensation products from the reaction of furfural with ketones and/or aldehydes.

DETAILED DESCRIPTION

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "organic compound" means a carbon-containing compound with the following exceptions: binary compounds as the carbon oxides, carbides, carbon disulfide, etc.; ternary compounds such as metallic cyanides, metallic carbonyls, phosgene, carbonylsulfide; and metallic carbonates such as calcium carbonate and sodium carbonate.

As used herein, the term "oxygenate" means an organic compound containing at least one oxygen atom. As used herein, the term "$C_n$ oxygenate" means an oxygenate containing n carbon atoms and, analogously, the term "$C_n$ diol" denotes a diol containing n carbon atoms.

As used herein, the term "biomass" refers to any cellulosic or lignocellulosic material and includes materials comprising hemicellulose, and optionally further comprising lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

As used herein, the term "hemicellulose" means a non-cellulosic polysaccharide found in lignocellulosic biomass. Hemicellulose is a branched heteropolymer consisting of different sugar monomers. It typically comprises from 500 to 3000 sugar monomeric units.

As used herein, the term "lignin" refers to a complex high molecular weight polymer that can comprise guaiacyl units, as in softwood lignin, or a mixture of guaiacyl and syringyl units, as in hardwood lignin.

As uses herein, the term "starch" refers to a carbohydrate consisting of a large number of glucose units joined by glycosidic bonds. Starch, also known as amylum, typically contains amylose and amylopectin.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; examples include xylose, arabinose, lyxose, and ribose. A hexose is a monosaccharide having six carbon atoms; examples include glucose and fructose. Disaccharide molecules consist of two covalently linked monosaccharide units; examples include sucrose, lactose, and maltose. As used herein, "oligosaccharide" molecules consist of about 3 to about 20 covalently linked monosaccharide units. Unless indicated otherwise herein, all references to specific sugars are intended to include the D-stereoisomer, the L-stereoisomer, and mixtures of the stereoisomers.

As used herein, the term "$C_n$ sugar" includes monosaccharides having n carbon atoms; disaccharides comprising monosaccharide units having n carbon atoms; and oligosaccharides comprising monosaccharide units having n carbon atoms. Thus, the term "$C_5$ sugar" includes pentoses, disaccharides comprising pentose units, and oligosaccharides comprising pentose units; the term "$C_6$ sugar" includes hexoses, disaccharides comprising hexose units, and oligosaccharides comprising hexose units.

As used herein, the term "$C_n$ sugar alcohol" refers to compounds produced from $C_n$ sugars by reduction of the carbonyl group to a primary or secondary hydroxyl group. Sugar alcohols having the general formula $H(HCHO)_{x+1}H$, are derived from sugars having the general formula $H(HCHO)_xHCO$. Monosaccharides and disaccharides can be used to form sugar alcohols, though the disaccharides are not fully hydrogenated. Three examples of sugar alcohols are xylitol ($C_5$), sorbitol ($C_6$), and mannitol ($C_6$).

As used herein, the abbreviation "16HD" refers to 1,6-hexanediol. The chemical structure of 1,6-hexanediol is represented by Formula (I).

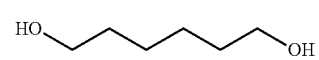

I

As used herein, the abbreviation "15PD" refers to 1,5-pentanediol. The chemical structure of 1,5-pentanediol is represented by Formula (II).

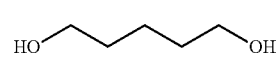

II

As used herein, the abbreviation "126HT" refers to 1,2,6-hexanetriol and includes a racemic mixture of isomers. The chemical structure of 1,2,6-hexanetriol is represented by Formula (III).

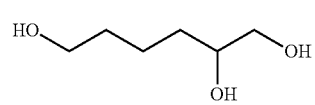

III

As used herein, the abbreviation "125PT" refers to 1,2,5-pentanetriol and includes a racemic mixture of isomers. The chemical structure of 1,2,5-pentanetriol is represented by Formula (IV).

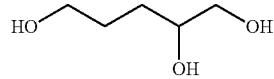

IV

As used herein, the abbreviation "Tetraol" refers to 1,2,5,6-tetrahydroxyhexane, also known as 3,4-dideoxyhexitol, and includes a mixture of stereoisomers. The chemical structure of 1,2,5,6-tetrahydroxyhexane is represented by Formula (V).

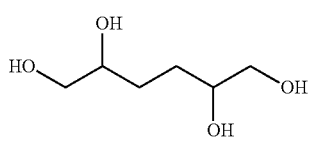

V

As used herein, the abbreviation "Pentaol" refers to 1,2,3,5,6-hexanepentaol and includes a racemic mixture of isomers. The chemical structure of 1,2,3,5,6-hexanepentaol is represented by Formula (VI).

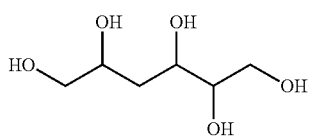

VI

As used herein, the abbreviation "THFdM" refers to tetrahydro-2,5-furandimethanol (also known as tetrahydrofuran-2,5-dimethanol or 2,5-tetrahydrofurandimethanol, or 2,5-bis[hydroxymethyl]tetrahydrofuran) and includes a mixture of stereoisomers (cis and racemic trans isomers). The chemical structure of tetrahydro-2,5-furandimethanol is represented by Formula (VII).

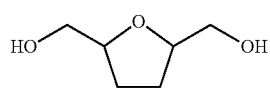

VII

The chemical structure of 2,5-dihydrofuran-2,5-dimethanol is represented by Formula (VIII).

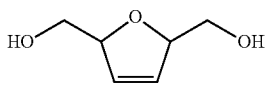

VIII

As used herein, the abbreviation "FdM" refers to 2,5-furandimethanol, also known as 2,5-bis(hydroxymethyl)furan. The chemical structure of 2,5-furandimethanol is represented by Formula (IX).

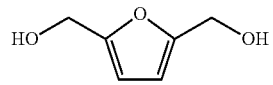

IX

The chemical structure of furfural, also known as furan-2-carbaldehyde or 2-furaldehyde, is represented by Formula (X).

X

The chemical structure of hydroxymethylfurfural, also known as 5-(hydroxymethyl)-2-furaldehyde, is represented by Formula (XI).

XI

The chemical structure of furfuryl alcohol, also known as 2-furanmethanol, is represented by Formula (XII).

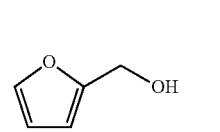

XII

The chemical structure of tetrahydrofurfuryl alcohol, also known as tetrahydro-2-furanmethanol, is represented by Formula (XIII).

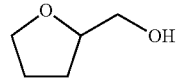

XIII

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (XIV).

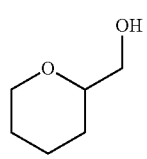

XIV

As used herein, the abbreviation "HOTHPM" refers to 2-hydroxymethyl-5-hydroxytetrahydro-2H-pyran, also known as 5-hydroxy-2H-tetrahydropyran-2 methanol or 1,5-anhydro-3,4-dideoxyhexitol, and includes a mixture of stereoisomers. The chemical structure of 2-hydroxymethyl-5-hydroxytetrahydro-2H-pyran is represented by Formula (XV).

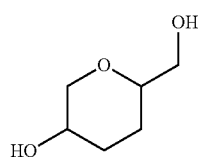

XV

The chemical structure of 3,4-dihydro-2H-pyran-2-carbaldehyde, also known as 3,4-dihydro-2H-pyran-2-carboxaldehyde, 2-formyl-3,4-dihydro-2H-pyran, or "acrolein dimer", is represented by Formula (XVI).

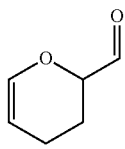

XVI

The chemical structure of levoglucosan, also known as 1,6-anhydro-β-glucopyranose, is represented by Formula (XVII).

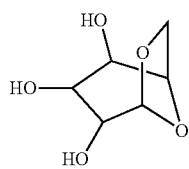

XVII

As used herein, the abbreviations "Lgone" and "LGone" refer to levoglucosenone, also known as 1,6-anhydro-3,4-dideoxy-β-D-pyranosen-2-one. The chemical structure of levoglucosenone is represented by Formula (XVIII).

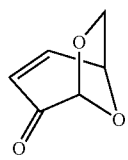

XVIII

The chemical structure of 1,6-anhydro-3,4-dideoxy-p-D-pyranose-2-one is represented by Formula (XIX).

XIX

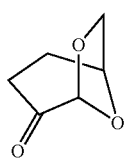

The chemical structure of levoglucosenol, also known as 1,6-anhydro-3,4-dideoxy-β-erythro-hex-3-enopyranose, is represented by Formula (XX).

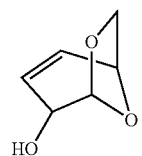

XX

As used herein, the abbreviations "Lgol" and "LGol" refer to levoglucosanol, also known as 1,6-anhydro-3,4-dideoxy-hexopyranose, and include a mixture of the threo and erythro stereoisomers. The chemical structure of 1,6-anhydro-3,4-dideoxyhexopyranose is represented by Formula (XXI).

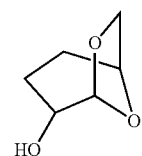

XXI

As used herein, the abbreviation "ISOS" refers to isosorbide, also known as 1,4:3,6-dianhydrosorbitol or 1,4-dianhydrosorbitol. The chemical structure of isosorbide is represented by Formula (XXII).

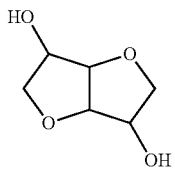

XXII

The chemical structure of sorbitol, also known as hexane-1,2,3,4,5,6-hexyl, is represented by Formula (XXIII).

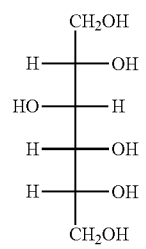

XXIII

The chemical structure of glucose, also known as dextrose or 2,3,4,5,6-pentahydroxyhexanal, is represented by Formula (XXIV).

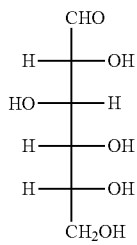

The chemical structure of fructose, also known as levulose, is represented by Formula (XXV).

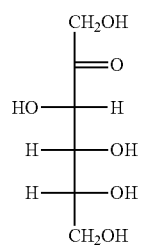

The chemical structure of xylitol, also known as pentane-1,2,3,4,5-pentol, is represented by Formula (XXVI).

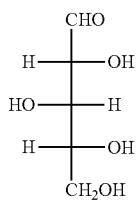

In one embodiment, a process is provided for preparing an $\alpha,\omega\text{-}C_n$-diol, the process comprising the steps:

(a) providing a feedstock comprising a $C_n$ oxygenate;

(b) contacting the feedstock with hydrogen gas, in the presence of a catalyst and at a temperature and for a time sufficient to form a product mixture comprising an $\alpha,\omega\text{-}C_n$-diol; wherein n is 5 or greater;

and wherein the catalyst comprises a first metal component, a heteropoly acid component, optionally a second metal component, optionally at least one promoter, and optionally a support; wherein the first metal component comprises Cu, Ni, Ir, Pt, Rh, Ru, Pd, Fe, Ag, or Au;

the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof;

the second metal component comprises Cr, a Cr oxide, Ni, a Ni oxide, Fe, a Fe oxide, Co, a Co oxide, Mn, a Mn oxide, Mo, a Mo oxide, W, a W oxide, Re, a Re oxide, Zn, a Zn oxide, $SiO_2$, or $Al_2O_3$; and the promoter comprises Na, K, Mg, Rb, Cs, Ca, Sr, Ba, Ce, or mixtures thereof.

In one embodiment, n=5 or 6. In one embodiment, n=5, and the $\alpha,\omega\text{-}C_n$-diol is 1,5-pentanediol. In one embodiment, n=6, and the $\alpha,\omega\text{-}C_n$-diol is 1,6-hexanediol. In one embodiment, n=7, and the $\alpha,\omega\text{-}C_n$-diol is 1,7-heptanediol. In one embodiment, n=8, and the $\alpha,\omega\text{-}C_n$-diol is 1,8-octanediol.

The first metal component is present in the catalyst in an amount ranging from about 0.1 to about 60 weight percent of the catalyst, for example from about 0.5 to about 20 weight percent of the catalyst. In one embodiment, the first metal component comprises Ni, Ir, Pt, Rh, Ru, Pd, Fe, Ag, or Au. In one embodiment, the first metal component comprises Ni, Pt, Pd, Fe, or Ru. In one embodiment, the first metal component comprises Ni or Fe. In one embodiment, the first metal component comprises Ir, Pt, Rh, Ru, or Pd. In one embodiment, the first metal component comprises Ni. In one embodiment, the first metal component comprises Pt. In one embodiment, the first metal component comprises Pd. In one embodiment, the first metal component comprises Fe. In one embodiment, the first metal component comprises Ru. In one embodiment, the first metal component comprises Ni or Fe and is present in the catalyst in an amount ranging from about 2 weight percent to about 60 weight percent, for example from about 5 weight percent to about 50 weight percent, or from about 5 weight percent to about 40 weight percent. In one embodiment, the first metal component comprises Ir, Pt, Rh, Ru, Pd, Ag, or Au and is present in the catalyst in an amount ranging from about 0.1 weight percent to about 15 weight percent, for example from about 0.1 weight percent to about 10 weight percent, or from about 0.25 weight percent to about 15 weight percent.

The heteropoly acid component comprises one or more heteropoly acids including, but not limited to, phosphotungstic acid $H_3[P(W_3O_{10})_4]$, silicotungstic acid $H_4[Si(W_3O_{10})_4]$, molybdophosphoric acid $H_4[P(Mo_3O_{10})_4]$, and silicomolybdic acid $H_4[Si(Mo_3O_{10})_4]$. The heteropoly acid component may include $H_4PW_{11}VO_{40}$. The heteropoly acid component can be used in the acid form (H+ cation), as a partially exchanged salt, or as a fully-exchanged salt. In one embodiment, the heteropoly acid component comprises partially cesium-exchanged, partially potassium-exchanged, partially rubidium-exchanged, or partially ammonium-exchanged salts of a heteropoly acid, or mixtures of two or more such salts. In one embodiment, the heteropoly acid component comprises one or more partially cesium-exchanged salts of a heteropoly acid, for example $Cs_{2.5}H_{0.5}[P(W_3O_{10})_4]$ or $Cs_{2.5}H_{0.5}[Si(W_3O_{10})_4]$. In one embodiment, the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, or $Cs_{2.5}H_{0.5}[Si(W_3O_{10})_4]$. In one embodiment, the heteropoly acid component comprises $H_3[P(W_3O_{10})_4]$, $H_4[Si(W_3O_{10})_4]$, or $Cs_{2.5}H_{0.5}[P(W_3O_{10})_4]$. The heteropoly acid component is present in the catalyst at a ratio of the first metal component to the heteropoly acid component in the range from about 9:1 to about 1:99 on a weight basis. In one embodiment, the ratio of the first metal component to the heteropoly acid component is in the range from about 2:1 to about 1:10 on a weight basis.

Optionally, a second metal component is present in the catalyst. In one embodiment the optional second metal component is present in the catalyst and comprises Cr, a Cr oxide, Ni, a Ni oxide, Fe, a Fe oxide, Co, a Co oxide, Mn, a Mn oxide, Mo, a Mo oxide, W, a W oxide, Re, a Re oxide, Zn, a Zn oxide, $SiO_2$, or $Al_2O_3$. In one embodiment the optional second metal component is present in the catalyst and comprises Cr, Ni, Fe, Co, Mn, Mo, W, Re, or Zn. In one embodiment the optional second metal component is present in the catalyst and comprises W or Re. The optional second metal component is present in an amount ranging from 0 to about 70, for example from 0 to about 50, or from 0 to about 25 weight percent of the catalyst. In one embodiment, the catalyst comprises a second metal component, and the second metal component is present in an amount ranging from about 1 to about 50, for example from about 1 to about 25, or from about 1 to about 15, or from about 1 to about 10, or from about 1 to about 5 weight percent of the catalyst.

Optionally, the catalyst comprises at least one promoter comprising Na, K, Mg, Rb, Cs, Ca, Sr, Ba, Ce, or mixtures thereof. In one embodiment, the optional promoter is present in the catalyst and comprises Cs. The promoter is present in the catalyst in an amount ranging from 0 to about 20 weight percent, for example from about 0 to about 15, or from about 1 to about 10, or from about 1 to about 5, weight percent. In one embodiment, the heteropoly acid component further comprises the promoter. In one embodiment, the first metal component further comprises the promoter. In one embodiment, the optional second metal component is present in the catalyst and comprises the promoter, for example as an oxide. In one embodiment, the optional support is present in the catalyst and comprises the promoter.

In one embodiment, the first metal component comprises Ni, Pt, Pd, Fe, or Ru; and the heteropoly acid component comprises $H_3[P(W_3O_{10})_4]$, $H_4[Si(W_3O_{10})_4]$, or $Cs_{2.5}H_{0.5}[P(W_3O_{10})_4]$. In one embodiment, the first metal component comprises Ni, Pt, Pd, Fe, or Ru; the heteropoly acid component comprises $H_3[P(W_3O_{10})_4]$, $H_4[Si(W_3O_{10})_4]$, or $Cs_{2.5}H_{0.5}[P(W_3O_{10})_4]$; and the optional second metal component is present in the catalyst and comprises W or Re.

The catalysts utilized in the processes described herein can be synthesized according to various methods. For example, a salt or oxide containing the first metal component can be mixed with a solution of the heteropoly acid component, the solvent (e.g., water) evaporated to dryness, and the resulting powder calcined. The optional second metal component, when present in the catalyst, can be added as a salt or oxide together with the salt or oxide containing the first metal component, or sequentially in an additional step. Alternatively, the heteropoly acid component may itself be provided as a solution of heteropolyacid and a basic salt, for example, a solution containing a mixture of $H_3[P(W_3O_{10})_4]$ and cesium carbonate in suitable proportions to form $Cs_{2.5}H_{0.5}[P(W_3O_{10})_4]$. In one catalyst preparation method, a support is added to an aqueous solution of a heteropoly acid, the solvent (e.g., water) evaporated to dryness, the resulting solid calcined, and the material then impregnated with a first metal, and optionally a second metal in sequence. Alternatively, the support can be added to an aqueous solution of a heteropoly acid, solids precipitated from the mixture by cesium carbonate addition, the solids calcined, then impregnated with a first metal, and optionally a second metal in sequence. Several synthetic methods are presented in the experimental section.

Catalyst preparation may further comprise drying catalyst materials under elevated temperatures from 30-250° C., preferably 50-150° C.; and/or calcination by heating in the presence of air at temperatures from 250-800° C., preferably 300-450° C.; and optionally reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

In some embodiments, it is useful to utilize a catalyst which comprises a support to enhance the stability and economic feasibility of the process. Examples of useful supports include $WO_3$, $SiO_2$, $Al_2O_3$, carbon, SiC, $TiO_2$, $ZrO_2$, $SiO_2$—$Al_2O_3$, clays such as montmorillonite, $SiO_2$—$TiO_2$, tungstated $ZrO_2$, $V_2O_5$, $MoO_3$, and zeolites such as H-Y, FAU (H-Y or USY), BEA (H-Beta), MFI (H-ZSM5), MEL (H-ZSM11) and MOR (H-Mordenite). Typically, tungstated $ZrO_2$ can comprise up to about 19 wt % W as $WO_3$ on $ZrO_2$, see for example S. Kuba et al in Journal of Catalysis 216 (2003), p. 353-361. In some embodiments, the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In some embodiments, the optional support is present in the catalyst and comprises $SiO_2$, $TiO_2$, zeolites, or mixtures thereof. In some embodiments, the solid support comprises $SiO_2$. In other embodiments, it may be desirable to not have a solid support.

The catalyst can be in any physical form typical for heterogeneous catalysts, including but not limited to: powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above.

Examples of $C_n$ oxygenates that are suitable for use in the present processes include 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxy-hexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes. The feedstock may comprise one or more Cn oxygenates.

In one embodiment, the $C_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof. These $C_n$ oxygenates are useful for preparation of reaction mixtures comprising 1,6-hexanediol by the processes disclosed herein. In one embodiment, the $C_n$ oxygenate comprises 1,2,6-hexanetriol.

In one embodiment, the $C_n$ oxygenate comprises 1,2,5-pentanetriol; furfural; furfuryl alcohol; tetrahydrofurfuryl alcohol; xylitol; or mixtures thereof. Such $C_n$ oxygenates are useful for preparation of product mixtures comprising 1,5-hexanediol by the processes disclosed herein.

Examples of suitable pentoses include without limitation xylose, arabinose, lyxose, xylitol, and ribose. Examples of suitable hexoses include without limitation glucose, mannose, fructose, and galactose. Examples of condensation products from the reaction of furfural or 5-(hydroxymethyl)-2-furfural with ketones and/or aldehydes are described in Synthesis (2008), (7), 1023-1028 (e.g., CAS Reg. No. 1040375-91-4 and CAS Reg. No. 886-77-1); and in ChemSusChem (2010), 3(10), 1158-1161, in which subjecting furfural and 5-(hydroxymethyl)-2-furfural to aldol condensation produced molecules having 8 to 15 carbon atoms.

Suitable $C_n$ oxygenates can be derived from biorenewable resources including biomass. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment, the $C_n$ oxygenate is ultimately derived from corn cobs, sugar cane bagasse, switchgrass, wheat straw, sawdust and other wood waste, and lignocellulosic feedstocks.

A biorenewable resource such as biomass can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research*, 71, 169-191 (1979)).

Glycerol can be obtained from a biorenewable resource, for example from hydrolysis of vegetable and animal fats and oils (that is, triacylglycerides comprising ester functionality resulting from the combination of glycerol with $C_{12}$ or greater fatty acids). 1,2,6-Hexanetriol can be obtained from materials such as glucose, cellulose or glycerol derived from a biorenewable resource. For example, 1,2,6-hexanetriol can be obtained by a process comprising the steps of contacting glycerol with a catalyst to prepare acrolein, heating acrolein (optionally in the presence of a catalyst) to prepare 2-formyl-3,4-dihydro-2H-pyran, contacting 2-formyl-3,4-dihydro-2H-pyran with water to prepare 2-hydroxyadipic aldehyde and contacting 2-hydroxyadipic aldehyde with hydrogen and a catalyst to produce a product mixture comprising 1,2,6-hexanetriol. See, for example, U.S. Pat. No. 2,768,213, German Patent No. 4238493, and L. Ott, et al. in *Green Chem.*, 2006, 8, 214-220.

The catalyst may be present in any weight ratio to the feedstock sufficient to catalyze the selective hydrodeoxygenation, generally in the range of 0.0001:1 to 1:1, preferably 0.001:1 to 0.5:1 for batch reactions. For continuous reactions, the same ratios are appropriate where the weight ratio of feed to catalyst is defined as weight of $C_n$ oxygenate feed processed per weight of catalyst.

Useful temperatures for the processes are between about 30° C. and about 300° C. In some embodiments, the temperature is between and optionally includes any two of the following values: 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., and 300° C. It is expected that with some catalysts, temperatures above about 300° C. could be used.

The process is conducted by contacting a Cn oxygenate feed with hydrogen in the presence of the catalyst for a time sufficient to form a product mixture comprising an $\alpha,\omega\text{-}C_n$-diol. The mole ratio of hydrogen to feed is not critical as long as sufficient hydrogen is present to produce the desired $\alpha,\omega\text{-}C_n$-diol. Hydrogen is preferably used in excess, and may optionally be used in combination with an inert gas such as nitrogen or argon. If an inert gas is used in combination with the hydrogen, the amount of the inert gas should be such that it does not negatively impact the formation of the product mixture. The pressure of the process may be between about 300 kPa and about 25,000 kPa. In some embodiments, the pressure of the process is between and optionally includes any two of the following values: 300; 500; 1000; 1500; 2000; 2500; 3000; 3500; 4000; 4500; 5000; 10,000; 15,000; 20,000; and 25,000 kPa.

The process is typically conducted in the presence of a solvent, which may serve to reduce the viscosity of the system to improve fluidity of the catalyst in the reaction vessel and/or to remove the heat of reaction and improve the performance of the process. Polar solvents are preferred. The solvent may be present in a range of 1% to 95% by weight of the total reaction mixture, excluding the catalyst.

The reaction products may be isolated or purified by any common methods known in the art including but not limited to distillation, wiped film evaporation, chromatography, adsorption, crystallization, and membrane separation.

It will be appreciated that the processes disclosed herein can also be utilized to prepare useful intermediates or byproducts in the synthesis of the $\alpha,\omega$-diols through optimization of the process parameters. Examples of intermediates that can be prepared during synthesis of 1,5-pentanediol and/or 1,6-hexanediol include but are not limited to furan dimethanol: tetrahydrofuran dimethanol; tetrahydropyran-2-methanol; levoglucosanol; and furfuryl alcohol. Examples of byproducts which can be obtained during synthesis of 1,5-pentanediol and/or 1,6-hexanediol include but are not limited to isomeric hexanols; isomeric pentanols; 1,5-hexanediol; 1,2-hexanediol; 2-methyltetrahydropyran; 2,5-dimethyltetrahydrofuran; 1,2-cyclohexanediol; 1,2-cyclopentanediol; cyclohexanol, and mixtures thereof.

The $\alpha,\omega\text{-}C_n$-diols obtained by the processes disclosed herein can be converted to industrially useful materials such as $\alpha,\omega\text{-}C_n$-diaminoalkanes. For example, 1,5-pentanediol and 1,6-hexanediol can be reductively aminated to 1,5-pentanediamine(1,5-diaminopentane) and 1,6-hexanediamine(1,6-diaminohexane), respectively, by methods known in the art. See, for example, U.S. Pat. No. 3,215,742; U.S. Pat. No. 3,268,588; and U.S. Pat. No. 3,270,059.

In some embodiments, the processes disclosed herein further comprise the steps:

(c) optionally, isolating the $\alpha,\omega\text{-}C_n$-diol from the product mixture;

(d) contacting the $\alpha,\omega\text{-}C_n$-diol with ammonia and hydrogen in the presence of a reductive amination catalyst at a temperature and for a time sufficient to form a second product mixture comprising an $\alpha,\omega\text{-}C_n$-diaminoalkane; and (e) optionally, isolating the $\alpha,\omega\text{-}C_n$-diaminoalkane from the second product mixture.

In one embodiment, the $\alpha,\omega\text{-}C_n$-diaminoalkane comprises 1,6-diaminohexane. In one embodiment, the $\alpha,\omega\text{-}C_n$-diaminoalkane comprises 1,5-diaminopentane.

The reductive amination catalyst contains at least one element selected from Groups IB, VIB, VIIB, and VIII of the Periodic Table, for example iron, cobalt, nickel, ruthenium, rhodium, palladium, osmium, copper, chromium, iridium, or platinum. The elements may be in the zero oxidation state or in the form of a chemical compound. The reductive amination catalyst may be supported, unsupported or Raney-type. In one embodiment, the reductive amination catalyst contains ruthenium. In one embodiment, the reductive amination catalyst contains nickel. In one embodiment, the reductive amination catalyst is Raney nickel. In one embodiment, the reductive amination catalyst is Raney copper. In one embodiment, the reductive amination catalyst is Raney cobalt.

The reductive amination step is conducted by contacting the α,ω-$C_n$-diol, or a product mixture comprising the α,ω-$C_n$-diol, with ammonia and hydrogen in the presence of the catalyst for a time sufficient to form a second product mixture comprising an α,ω-$C_n$-diaminoalkane. Useful temperatures for the reductive amination step are in the range of about 40° C. to 300° C., for example in the range of about 75° C. to 150° C. Typically pressures are in the range of about 2 MPa to 35 MPa, for example in the range of about 4 MPa to 12 MPa. The molar ratio of hydrogen to the α,ω-$C_n$-diol is typically equal to or greater than 1:1, for example in the range of 1:1 to 100:1, or in the range of 1:1 to 50:1.

The reductive amination step is typically performed in liquid ammonia solvent. The ammonia is used in stoichiometric excess with reference to the α,ω-$C_n$-diol. Typically, a molar ratio of 1:1 to 80:1 of ammonia to the α,ω-$C_n$-diol can be used, for example a molar ratio in the range of 10:1 to 50:1. Optionally, an additional solvent such as water, methanol, ethanol, butanol, pentanol, hexanol, an, ester, a hydrocarbon, tetrahydrofuran, or dioxane, can be used. The weight ratio of the additional solvent to the α,ω-$C_n$-diol is typically in the range of 0.1:1 to 5:1.

The reductive amination step can be performed in a fixed bed reactor or in a slurry reactor, for example a batch, continuous stirred tank reactor or bubble column reactor. The α,ω-$C_n$-diamine may be isolated from the second product mixture by any common methods known in the art, for example fractional distillation under moderate vacuum.

EXAMPLES

The processes described herein are illustrated in the following examples. From the above discussion and these examples, one skilled in the art can ascertain the essential characteristics of this invention, and without departing from the spirit and scope thereof, can make various changes and modifications to adapt it to various uses and conditions.

The following abbreviations are used in the examples: "° C." means degrees Celsius; "wt %" means weight percent; "g" means gram; "mg" means milligrams; "m²/g" means square meters per gram; "psi" means pounds per square inch; "mL" means milliliter; "M" means mole/liter; "mL/min" means milliliter(s) per minute; "h" means hour(s); "kPa" means kilopascal; "ID" means internal diameter; "cm" means centimeter(s); "GC" means gas chromatography; "Temp" means temperature; "Ex" means Example, "Comp Ex" means Comparative Example; "conv" means conversion; "sel" means selectivity, "MPa" means megapascal(s); "GC" means gas chromatography; "MS" means "mass spectrometry"; "LHSV" means liquid hourly space velocity; "GTO" means gas to oil ratio; "12HD" means 1,2-hexanediol; "12CHD" means 1,2-cyclohexanediol; "c12CHD" means cis-1,2-cyclohexanediol; "1H" means 1-hexanol; "1P" means 1-pentanol; "15HD" means 1,5-hexanediol.

Percent conversion and percent yield are defined as follows, where the mol of compounds are determined from calibrated gas chromatographic methods:

$$\% \text{ Conversion} = \frac{100 * (\text{mol starting material charged} - \text{mol starting material remaining})}{\text{mol starting material charged}}$$

$$\% \text{ Yield} = \frac{100 * \text{mol product compound}}{\text{mol starting material charged}}$$

$Cs_2CO_3$, $H_3PW_{12}O_{40} \cdot (H_2O)_x$, $H_4SiW_{12}O_{40} \cdot (H_2O)_x$ and tetraammineplatinum (II) nitrate were purchased from Sigma-Aldrich (St. Louis, Mo.). Palladium nitrate was purchased from Alfa Aesar (Ward Hill, Mass.).

1,2,6-Hexanetriol (greater than 97 GC area % purity) was obtained from Evonik DEGUSSA GmBH, Marl, Germany. Tetrahydrofuran-2,5-dimethanol (97% purity) was obtained from Aldrich. 2-Hydroxymethyltetrahydropyran (98% purity) was obtained from Aldrich.

All catalysts were calcined in air unless indicated otherwise.

Catalyst Preparation Method A

Preparation of Pd and Pt Catalysts Comprising Partially Cs-Exchanged Heteropoly Acids Catalysts $PdCs_{2.5}H_{0.5}PW_{12}O_{40}$ and $PtCs_{2.5}H_{0.5}PW_{12}O_{40}$ were prepared by mixing a soluble metal salt in an aqueous heteropolyacid solution then co-precipitating the heteropoly acid with $Cs_2CO_3$ according to the following procedure.

The heteropolyacid $H_3PW_{12}O_{40}$ was prepared for use in aqueous solution by first dehydrating it at 60° C. under a vacuum for 2 hours. $Cs_2CO_3$ was dehydrated at 420° C. for 2 hours under a vacuum prior to its use for preparing an aqueous solution.

The desired amount of tetraammineplatinum (II) nitrate or palladium nitrate (selected to give a 1:100 weight ratio of Pd:$Cs_{2.5}H_{0.5}PW_{12}O_{40}$ and a 1.5:100 weight ratio of Pt:$Cs_{2.5}H_{0.5}PW_{12}O_{40}$) was dissolved in the aqueous solution of $H_3PW_{12}O_{40}$ (0.08 mol/L). This mixture was then titrated with an aqueous solution of $Cs_2CO_3$ (0.25 mol/L) at room temperature at a rate of 1 mL/minute. The resulting colloidal suspension was evaporated to a solid at 50° C. under a vacuum. The solids were then placed in a 120° C. vacuum oven for 2 hours to remove water. The dried solids were calcined in air at 300° C. for 1 hour.

Example 1

Hydrodeoxygenation of 1,2,6-hexanetriol using $PdCs_{2.5}H_{0.5}PW_{12}O_{40}$ Catalyst Prepared by Method A A 5% wt solution of 126HT in water was combined with about 50 mg of $PdCs_{2.5}H_{0.5}PW_{12}O_{40}$ in a glass vial equipped with a magnetic stir bar. The vial was capped with a perforated septum to limit vapor transfer rates. Next, the capped vial was placed in a stainless steel (SS316) parallel pressure reactor having 8 individual wells. The reactor was then connected to a high pressure gas manifold and purged with nitrogen gas (1000 psi) three times. About 800 psi of hydrogen was then added and the reactor was heated to 250° C.; the hydrogen pressure in the reactor was adjusted to about 1000 psi. These conditions were held for 4 hours.

The reactor was then allowed to cool to room temperature and the pressure was released. The reaction solution was diluted with n-propanol containing an internal standard, filtered through a 5-micron disposable filter, and analyzed by GC (and in some cases by GC/MS) using an internal standard method for quantitative analysis. Results are presented in Table 1.

Example 2

Hydrodeoxygenation of 1,2,6-hexanetriol using PtCs$_{2.5}$H$_{0.5}$PW$_{12}$O$_{40}$ Catalyst Prepared by Method A Example 2 was performed as for Example 1, except that PtCs$_{2.5}$H$_{0.5}$PW$_{12}$O$_{40}$ was used as the catalyst. Results are presented in Table 1.

TABLE 1

Hydrodeoxygenation Results for PdCs$_{2.5}$H$_{0.5}$PW$_{12}$O$_{40}$ and PtCs$_{2.5}$H$_{0.5}$PW$_{12}$O$_{40}$ Catalysts

| Ex | Metal Component A | Heteropoly Acid Component B | Ratio A:B (wt) | Conv (%) | Yield (%) | | | | |
|---|---|---|---|---|---|---|---|---|---|
| | | | | | 16HD | THPM | 12HD | 12CHD* | 1H |
| 1 | Pd | Cs$_{2.5}$H$_{0.5}$PW$_{12}$O$_{40}$ | 1:100 | 8 | 2 | 5 | 1 | <1 | <1 |
| 2 | Pt | Cs$_{2.5}$H$_{0.5}$PW$_{12}$O$_{40}$ | 1.5:100 | 100 | 25 | 9 | <1 | <1 | 17 |

*12CHD yield reported as the sum of cis- and trans- isomers

Preparation of Cs$_{2.5}$H$_{0.5}$PW$_{12}$O$_{40}$

The partially Cs-exchanged salt of the tungsten heteropoly acid was prepared using an aqueous solution of Cs$_2$CO$_3$ and an aqueous solution of H$_3$PW$_{12}$O$_{40}$. The heteropolyacid H$_3$PW$_{12}$O$_{40}$ was prepared for use in aqueous solution by first dehydrating it at 60° C. under vacuum for 2 hours. Cs$_2$CO$_3$ was dehydrated at 420° C. for 2 hours under vacuum prior to its use for preparing an aqueous solution.

An aqueous solution of H$_3$PW$_{12}$O$_{40}$ (0.08 mol/L) was titrated with an aqueous solution of Cs$_2$CO$_3$ (0.25 mol/L) at room temperature at a rate of 1 mL/minute. The resulting white colloidal suspension was evaporated to a solid at 50° C. under vacuum. The solids were then placed in a 120° C. vacuum oven for 2 hours to remove water. The dried solids were calcined in air at 300° C. for 1 hour.

Preparation of Partially Cesium-Exchanged Heteropoly Acid Cs$_{2.5}$H$_{0.5}$PW$_{12}$O$_{40}$ (15% wt) on SiO$_2$ The partially Cs-exchanged salt of the tungsten heteropoly acid was prepared using an aqueous solution of Cs$_2$CO$_3$ and SiO$_2$ (Silica Gel 60, EMD, Darmstadt Germany) suspended in an aqueous solution of H$_3$PW$_{12}$O$_{40}$. The heteropoly acid H$_3$PW$_{12}$O$_{40}$ was prepared for use in aqueous solution by first dehydrating it at 60° C. under vacuum for 2 hours. Cs$_2$CO$_3$ was dehydrated at 420° C. for 2 hours under vacuum prior to its use for preparing an aqueous solution, and SiO$_2$ was used as received.

SiO$_2$ (83.1 wt. parts) was suspended in a solution of 13.2 wt. parts of H$_3$PW$_{12}$O$_{40}$ in water (0.08 mol/L). This suspension was titrated with a solution of 3.7 wt. parts Cs$_2$CO$_3$ (0.25 mol/L) in water at room temperature at a rate of 1 mL/minute. The resulting white colloidal suspension was evaporated to a solid at 50° C. under vacuum. The solids were then placed in a 120° C. vacuum oven for 2 hours to remove water. The dried solids were calcined in air at 300° C. for 1 hour.

The Cs$_{2.5}$H$_{0.5}$PW$_{12}$O$_{40}$ and 15% Cs$_{2.5}$H$_{0.5}$PW$_{12}$O$_{40}$/SiO$_2$ prepared as described were used to prepare M1 and M1M2/heteropoly acid and M1/heteropoly acid catalysts as described below.

Catalyst Preparation Method B

Preparation of M1M2/Heteropoly Acid Catalysts

A PtW/Cs$_{2.5}$H$_{0.5}$P(W$_3$O$_{10}$)$_4$ catalyst containing 4% Pt and a W/Pt weight ratio of 0.25 was prepared as follows. 0.92 g of Cs$_{2.5}$H$_{0.5}$P(W$_3$O$_{10}$)$_4$ (prepared as described herein above) that had been ground with a mortar and pestle and passed through a 400 microns mesh sieve was impregnated with 0.079 g of tetraammineplatinum (II) nitrate dissolved in 1.0 mL of water. The resulting slurry was mixed for 15 minutes, then dried overnight in a vacuum oven at 110° C. The resulting solid was allowed to cool to room temperature, and then wetted with 1.0 mL of water. To this was added 0.0133 g of ammonium tungsten oxide hydrate dissolved in 3.0 mL of water. The resulting mixture was stirred for 15 minutes. The material was then placed into a vacuum oven and dried overnight at 110° C. After cooling to room temperature, the material was transferred to a ceramic boat and calcined in air at 350° C. for three hours.

Additional catalysts containing a first metal component, a second metal component, a heteropoly acid, and cesium as a promoter were prepared by sequentially impregnating a partially cesium-exchanged heteropoly acid with two different metals using the general procedure detailed above, but with appropriate changes to the M1-containing salt, the M2-containing salt, and the amounts of each metal salt and the partially cesium-exchanged heteropoly acid. In this way catalysts containing the partially cesium-exchanged heteropoly acid and 1 wt %, 2.5 wt %, 4 wt % or 10 wt % M1 with a M2/M1 weight ratio of 0.25, 1.63, or 3.0 were prepared. The metal salts used to prepare these catalysts are given in Table 2.

The catalysts prepared according to Method B were used in Examples 3, 4, 8-12, 18-23, 27-31, 37, 39-44, 47, and 51. Results are presented in Tables 3, 4, 5, 6, and 7.

TABLE 2

Commercially Available Metal Salts Used in Catalyst Preparation

| Metal Salt | Source |
|---|---|
| Rhodium (III) Chloride Hydrate | Strem |
| Ruthenium (III) Chloride Hydrate | Alfa Aesar |
| Copper (II) Nitrate Hydrate | Alfa Aesar |
| Palladium Nitrate | Alfa Aesar |
| Nickel (II) nitrate Hexahydrate | Aldrich |
| Iridium (IV) Chloride Hydrate | Aldrich |
| Silver Nitrate | Aldrich |
| Iron (III) Nitrate Nonahydrate | Aldrich |
| Ammonium Perhenate | Aldrich |
| Ammonium Tungsten Oxide Hydrate | Alfa Aesar |
| Hydrogen Tetrachloroaurate (III) hydrate | Aldrich |

Catalyst Preparation Method C

Preparation of M1/Heteropoly Acid Catalysts

A Pt/Cs$_{2.5}$H$_{0.5}$P(W$_3$O$_{10}$)$_4$ catalyst containing 4 wt % Pt was prepared as follows. 0.48 g of Cs$_{2.5}$H$_{0.5}$P(W$_3$O$_{10}$)$_4$ (prepared as described herein above) that had been ground with a mortar and pestle and passed through a 400 microns mesh sieve was impregnated with 0.0396 g of tetraammineplatinum (II) nitrate in 1.0 mL of water. The resulting slurry was mixed for 15 minutes, then dried overnight in a vacuum oven at 110° C. After cooling to room temperature, the material was transferred to a ceramic boat and calcined in air at 350° C. for three hours.

Additional catalysts containing a first metal component, a heteropoly acid, and cesium as a promoter were prepared by impregnating a partially cesium-exchanged heteropoly acid with a metal using the general procedure detailed above, but with appropriate changes to the M1-containing salt and the amounts of the metal salt and the partially cesium-exchanged heteropoly acid. In this way catalysts containing the partially cesium-exchanged heteropoly acid and 1 wt %, 2.5 wt %, 4 wt %, 10 wt %, or 20 wt % M1 were prepared. The metal salts used to prepare these catalysts are given in Table 2.

The catalysts prepared according to Method C were used in Examples 5, 6, 7, 13-16, 24, 25, 32-36, 38, 45, 46, 48-50, and 52-60. Results are presented in Tables 3-7.

Catalyst Preparation Method D

Preparation of Supported Catalysts Pt/15% Cs$_{2.5}$H$_{0.5}$PW$_{12}$O$_{40}$/SiO$_2$ and Fe/15% Cs$_{2.5}$H$_{0.5}$PW$_{12}$O$_{40}$/SiO$_2$ Catalysts A Pt/15% Cs$_{2.5}$H$_{0.5}$PW$_{12}$O$_{40}$/SiO$_2$ catalyst containing 4 wt % Pt was prepared as follows. 0.48 g of 15% Cs$_{2.5}$H$_{0.5}$PW$_{12}$O$_{40}$/SiO$_2$ (prepared as described herein above) that had been ground with a mortar and pestle and passed through a 400 microns mesh sieve was impregnated with 0.0396 g of tetraammineplatinum (II) nitrate in 1.0 mL of water. The resulting slurry was mixed for 15 minutes, then dried overnight in a vacuum oven at 110° C. After cooling to room temperature, the material was transferred to a ceramic boat and calcined in air at 350° C. for three hours.

A Fe/15% Cs$_{2.5}$H$_{0.5}$PW$_{12}$O$_{40}$/SiO$_2$ catalyst containing 4 wt % Fe was prepared following the same procedure except using 0.48 g of 15% Cs$_{2.5}$H$_{0.5}$PW$_{12}$O$_{40}$/SiO$_2$ and 0.137 g of iron(III) nitrate nonahydrate.

The catalysts prepared according to Method D were used in Examples 17 and 26. Results are presented in Tables 3 and 4.

Examples 3-60

Hydrodeoxygenation of 1,2,6-hexanetriol

Each catalyst prepared according to Method B, C, or D was used to hydrodeoxygenate 1,2,6-hexanetriol to a product mixture comprising 1,6-hexanediol following the procedure of Example 1, except that for each Example the reactor was heated to the temperature indicated in the following Tables.

The data in Table 3 through Table 7 show conversion and yields to selected components of the product mixtures obtained using catalysts comprising a first metal component, a heteropoly acid component, a Cs promoter, optionally a second metal component, and optionally a support under the indicated reaction conditions.

TABLE 3

Hydrodeoxygenation Results for Catalysts Containing Pt or PtW

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 3 | 140 | PtW/CS$_{2.5}$H$_{0.5}$P(W$_3$O$_{10}$)$_4$ | Pt | 4.0 | W | 0.25 | 100.0 | 57.8 | 0.6 | 0.2 | 26.9 |
| 4 | 140 | PtW/CS$_{2.5}$H$_{0.5}$P(W$_3$O$_{10}$)$_4$ | Pt | 4.0 | W | 3.00 | 22.5 | 14.8 | 3.2 | 0.2 | 3.1 |
| 5 | 140 | Pt/Cs$_{2.5}$H$_{0.5}$P(W$_3$O$_{10}$)$_4$ | Pt | 1.0 | — | 0 | 17.6 | 12.4 | 4.0 | 0.2 | 0.2 |
| 6 | 140 | Pt/Cs$_{2.5}$H$_{0.5}$P(W$_3$O$_{10}$)$_4$ | Pt | 2.5 | — | 0 | 68.7 | 51.2 | 2.8 | 0.1 | 4.9 |
| 7 | 140 | Pt/Cs$_{2.5}$H$_{0.5}$P(W$_3$O$_{10}$)$_4$ | Pt | 4.0 | — | 0 | 100.0 | 61.7 | 1.1 | 0.1 | 19.6 |
| 8 | 160 | PtW/Cs$_{2.5}$H$_{0.5}$P(W$_3$O$_{10}$)$_4$ | Pt | 1.0 | W | 3.00 | 18.4 | 8.1 | 9.0 | 0.2 | 1.5 |
| 9 | 160 | PtW/Cs$_{2.5}$H$_{0.5}$P(W$_3$O$_{10}$)$_4$ | Pt | 1.0 | W | 0.25 | 45.1 | 31.1 | 7.2 | 0.2 | 3.0 |
| 10 | 160 | PtW/Cs$_{2.5}$H$_{0.5}$P(W$_3$O$_{10}$)$_4$ | Pt | 2.5 | W | 1.63 | 86.3 | 54.0 | 5.1 | 0.2 | 11.2 |
| 11 | 160 | PtW/Cs$_{2.5}$H$_{0.5}$P(W$_3$O$_{10}$)$_4$ | Pt | 4.0 | W | 0.25 | 100.0 | 46.7 | 1.1 | 0.1 | 26.9 |
| 12 | 160 | PtW/Cs$_{2.5}$H$_{0.5}$P(W$_3$O$_{10}$)$_4$ | Pt | 4.0 | W | 3.00 | 52.7 | 25.0 | 8.0 | 0.2 | 4.9 |
| 13 | 160 | Pt/Cs$_{2.5}$H$_{0.5}$P(W$_3$O$_{10}$)$_4$ | Pt | 1.0 | — | — | 45.1 | 23.4 | 7.6 | 0.2 | 2.7 |
| 14 | 160 | Pt/Cs$_{2.5}$H$_{0.5}$P(W$_3$O$_{10}$)$_4$ | Pt | 2.5 | — | — | 100.0 | 54.3 | 2.9 | 0.2 | 17.8 |
| 15 | 160 | Pt/Cs$_{2.5}$H$_{0.5}$P(W$_3$O$_{10}$)$_4$ | Pt | 4.0 | — | — | 100.0 | 46.8 | 1.1 | 0.2 | 23.2 |
| 16 | 250 | Pt/Cs$_{2.5}$H$_{0.5}$P(W$_3$O$_{10}$)$_4$ | Pt | 4.0 | — | — | 100.0 | 0.2 | 0.6 | 0.0 | 2.4 |
| 17 | 250 | Pt/15 wt % Cs$_{2.5}$H$_{0.5}$P(W$_3$O$_{10}$)$_4$ on SiO$_2$ | Pt | 4.0 | — | — | 90.3 | 31.3 | 11.2 | 0.4 | 7.2 |

TABLE 4

Hydrodeoxygenation Results for Catalysts Containing Fe or FeW

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 18 | 250 | FeW/Cs$_{2.5}$H$_{0.5}$P(W$_3$O$_{10}$)$_4$ | Fe | 4 | W | 1 | 100.0 | 6.3 | 14.8 | 7.2 | 0.9 |
| 19 | 250 | FeW/Cs$_{2.5}$H$_{0.5}$P(W$_3$O$_{10}$)$_4$ | Fe | 10 | W | 1 | 100.0 | 4.3 | 21.2 | 20.6 | 0.9 |

TABLE 4-continued

Hydrodeoxygenation Results for Catalysts Containing Fe or FeW

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 20 | 200 | FeW/Cs$_{2.5}$H$_{0.5}$P(W$_3$O$_{10}$)$_4$ | Fe | 4 | W | 1 | 52.7 | 1.7 | 22.6 | 0.0 | 0.9 |
| 21 | 200 | FeW/Cs$_{2.5}$H$_{0.5}$P(W$_3$O$_{10}$)$_4$ | Fe | 10 | W | 1 | 36.7 | 1.9 | 13.2 | 6.5 | 0.9 |
| 22 | 220 | FeW/Cs$_{2.5}$H$_{0.5}$P(W$_3$O$_{10}$)$_4$ | Fe | 4 | W | 1 | 100.0 | 6.7 | 30.5 | 14.8 | 1.9 |
| 23 | 220 | FeW/Cs$_{2.5}$H$_{0.5}$P(W$_3$O$_{10}$)$_4$ | Fe | 10 | W | 1 | 87.0 | 10.7 | 28.1 | 14.5 | 1.6 |
| 24 | 250 | Fe/Cs$_{2.5}$H$_{0.5}$P(W$_3$O$_{10}$)$_4$ | Fe | 10 | — | — | 20.1 | 2.7 | 8.4 | 2.6 | 1.5 |
| 25 | 250 | Fe/Cs$_{2.5}$H$_{0.5}$P(W$_3$O$_{10}$)$_4$ | Fe | 4 | — | — | 100.0 | 0.5 | 4.8 | 1.0 | 0.7 |
| 26 | 250 | Fe/15 wt % Cs$_{2.5}$H$_{0.5}$P(W$_3$O$_{10}$)$_4$ on SiO$_2$ | Fe | 4 | — | — | 8.0 | 1.7 | 6.2 | 0.4 | 0.6 |

TABLE 5

Hydrodeoxygenation Results for Catalysts Containing Ni or NiW

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 27 | 250 | NiW/Cs$_{2.5}$H$_{0.5}$P(W$_3$O$_{10}$)$_4$ | Ni | 4 | W | 1 | 100.0 | 16.6 | 14.5 | 4.3 | 1.7 |
| 28 | 250 | NiW/Cs$_{2.5}$H$_{0.5}$P(W$_3$O$_{10}$)$_4$ | Ni | 10 | W | 1 | 88.6 | 37.1 | 21.9 | 2.3 | 2.6 |
| 29 | 200 | NiW/Cs$_{2.5}$H$_{0.5}$P(W$_3$O$_{10}$)$_4$ | Ni | 4 | W | 1 | 34.0 | 6.0 | 9.6 | 1.7 | 0.5 |
| 30 | 220 | NiW/Cs$_{2.5}$H$_{0.5}$P(W$_3$O$_{10}$)$_4$ | Ni | 4 | W | 1 | 56.5 | 22.8 | 24.8 | 4.4 | 2.6 |
| 31 | 220 | NiW/Cs$_{2.5}$H$_{0.5}$P(W$_3$O$_{10}$)$_4$ | Ni | 10 | W | 1 | 31.1 | 13.9 | 16.6 | 4.0 | 1.6 |
| 32 | 250 | Ni/Cs$_{2.5}$H$_{0.5}$P(W$_3$O$_{10}$)$_4$ | Ni | 20 | — | — | 99.2 | 33.8 | 20.5 | 0.9 | 0.1 |
| 33 | 250 | Ni/Cs$_{2.5}$H$_{0.5}$P(W$_3$O$_{10}$)$_4$ | Ni | 10 | — | — | 38.0 | 19.1 | 15.3 | 4.4 | 0.0 |
| 34 | 250 | Ni/Cs$_{2.5}$H$_{0.5}$P(W$_3$O$_{10}$)$_4$ | Ni | 10 | — | — | 100.0 | 8.1 | 13.1 | 11.7 | 0.0 |
| 25 | 200 | Ni/Cs$_{2.5}$H$_{0.5}$P(W$_3$O$_{10}$)$_4$ | Ni | 10 | — | — | 8.1 | 3.4 | 8.8 | 0.3 | 0.5 |
| 36 | 180 | Ni/Cs$_{2.5}$H$_{0.5}$P(W$_3$O$_{10}$)$_4$ | Ni | 10 | — | — | 8.2 | 0.5 | 4.0 | 0.0 | 0.6 |
| 37 | 180 | NiW/Cs$_{2.5}$H$_{0.5}$P(W$_3$O$_{10}$)$_4$ | Ni | 10 | W | 1 | 10.2 | 1.2 | 5.7 | 0.0 | 1.1 |
| 38 | 250 | Ni/Cs$_{2.5}$H$_{0.5}$P(W$_3$O$_{10}$)$_4$ | Ni | 4 | — | — | 100.0 | 13.4 | 12.1 | 1.3 | 3.4 |

TABLE 6

Hydrodeoxygenation Results for Catalysts Containing Pd or PdW

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 39 | 250 | PdW/Cs$_{2.5}$H$_{0.5}$P(W$_3$O$_{10}$)$_4$ | Pd | 4 | W | 1 | 100.0 | 14.2 | 13.6 | 1.0 | 10.7 |
| 40 | 250 | PdW/Cs$_{2.5}$H$_{0.5}$P(W$_3$O$_{10}$)$_4$ | Pd | 10 | W | 1 | 100.0 | 22.2 | 21.2 | 0.7 | 8.2 |
| 41 | 200 | PdW/Cs$_{2.5}$H$_{0.5}$P(W$_3$O$_{10}$)$_4$ | Pd | 4 | W | 1 | 76.3 | 19.3 | 30.2 | 0.5 | 6.7 |
| 42 | 200 | PdW/Cs$_{2.5}$H$_{0.5}$P(W$_3$O$_{10}$)$_4$ | Pd | 10 | W | 1 | 59.0 | 13.9 | 23.5 | 0.4 | 4.3 |
| 43 | 220 | PdW/Cs$_{2.5}$H$_{0.5}$P(W$_3$O$_{10}$)$_4$ | Pd | 4 | W | 1 | 100.0 | 26.6 | 28.9 | 0.0 | 7.9 |
| 44 | 220 | PdW/Cs$_{2.5}$H$_{0.5}$P(W$_3$O$_{10}$)$_4$ | Pd | 10 | W | 1 | 89.8 | 24.9 | 29.4 | 0.6 | 8.0 |
| 45 | 250 | Pd/Cs$_{2.5}$H$_{0.5}$P(W$_3$O$_{10}$)$_4$ | Pd | 10 | — | — | 100.0 | 2.1 | 2.4 | 0.1 | 8.2 |
| 46 | 250 | Pd/Cs$_{2.5}$H$_{0.5}$P(W$_3$O$_{10}$)$_4$ | Pd | 20 | — | — | 100.0 | 3.3 | 4.0 | 0.0 | 7.8 |

TABLE 7

Hydrodeoxygenation Results for Catalysts Containing Ag, Ru, Rh, Ir, RhRe, or IrRe

| Ex | Temp (° C.) | Catalyst | M1 | M1 wt % | M2 | M2/M1 molar ratio | Conversion (%) | Yield (%) 16HD | THPM | 12HD | 1H |
|---|---|---|---|---|---|---|---|---|---|---|---|
| 47 | 160 | IrRe/Cs$_{2.5}$H$_{0.5}$P(W$_3$O$_{10}$)$_4$ | Ir | 4 | Re | 1 | 79.2 | 25.2 | 11.3 | 0.0 | 13.5 |
| 48 | 250 | Ir/Cs$_{2.5}$H$_{0.5}$P(W$_3$O$_{10}$)$_4$ | Ir | 4 | — | — | 100.0 | 0.4 | 0.9 | 0.0 | 0.0 |
| 49 | 200 | Ir/Cs$_{2.5}$H$_{0.5}$P(W$_3$O$_{10}$)$_4$ | Ir | 4 | — | — | 100.0 | 17.4 | 9.2 | 0.0 | 30.6 |
| 50 | 180 | Ir/Cs$_{2.5}$H$_{0.5}$P(W$_3$O$_{10}$)$_4$ | Ir | 4 | — | — | 100.0 | 22.6 | 9.3 | 0.0 | 24.3 |
| 51 | 160 | RhRe/Cs$_{2.5}$H$_{0.5}$P(W$_3$O$_{10}$)$_4$ | Rh | 4 | Re | 1 | 98.5 | 17.3 | 1.1 | 0.0 | 26.2 |
| 52 | 250 | Rh/Cs$_{2.5}$H$_{0.5}$P(W$_3$O$_{10}$)$_4$ | Rh | 4 | — | — | 100.0 | 0.0 | 0.5 | 0.0 | 0.0 |
| 53 | 200 | Rh/Cs$_{2.5}$H$_{0.5}$P(W$_3$O$_{10}$)$_4$ | Rh | 4 | — | — | 100.0 | 1.3 | 2.8 | 0.0 | 2.1 |
| 54 | 180 | Rh/Cs$_{2.5}$H$_{0.5}$P(W$_3$O$_{10}$)$_4$ | Rh | 4 | — | — | 100.0 | 0.3 | 1.9 | 0.0 | 3.9 |
| 55 | 250 | Ru/Cs$_{2.5}$H$_{0.5}$P(W$_3$O$_{10}$)$_4$ | Ru | 4 | — | — | 100.0 | 1.4 | 2.6 | 1.0 | 0.0 |

TABLE 7-continued

Hydrodeoxygenation Results for Catalysts Containing Ag, Ru, Rh, Ir, RhRe, or IrRe

| Ex | Temp (° C.) | Catalyst | M1 | M1 wt % | M2 | M2/M1 molar ratio | Conversion (%) | Yield (%) 16HD | THPM | 12HD | 1H |
|----|------|------|------|------|------|------|------|------|------|------|------|
| 56 | 200 | Ru/Cs$_{2.5}$H$_{0.5}$P(W$_3$O$_{10}$)$_4$ | Ru | 4 | — | — | 66.9 | 28.0 | 28.7 | 0.0 | 5.7 |
| 57 | 180 | Ru/Cs$_{2.5}$H$_{0.5}$P(W$_3$O$_{10}$)$_4$ | Ru | 4 | — | — | 52.5 | 16.2 | 21.2 | 0.0 | 3.7 |
| 58 | 250 | Ag/Cs$_{2.5}$H$_{0.5}$P(W$_3$O$_{10}$)$_4$ | Ag | 4 | — | — | 100.0 | 0.5 | 2.9 | 2.6 | 0.0 |
| 59 | 200 | Ag/Cs$_{2.5}$H$_{0.5}$P(W$_3$O$_{10}$)$_4$ | Ag | 4 | — | — | 100.0 | 3.9 | 32.7 | 0.0 | 1.3 |
| 60 | 180 | Ag/Cs$_{2.5}$H$_{0.5}$P(W$_3$O$_{10}$)$_4$ | Ag | 4 | — | — | 64.5 | 4.3 | 24.4 | 0.0 | 2.8 |

Impregnation of Supports with Silica Tungstic Acid

Titanium dioxide impregnated with 10 weight percent silica tungstic acid hydrate, based on the total weight of support and silica tungstic acid hydrate was prepared as follows.

An aqueous solution of silica tungstic acid hydrate (Aldrich) (0.300 g dissolved in 3.0 mL of water) was added to 2.70 g of Aerolyst 7711 TiO$_2$ (Evonik) that had been passed through a 400 micron mesh sieve prior to wetting with water (4.0 mL). The resulting slurry was stirred at room temperature for 24 hours, and then dried overnight in a vacuum oven at 110° C. The solid material was allowed to cool to room temperature, then transferred to a ceramic boat and calcined in air at 350° C. for 5 hours.

SiO$_2$ (EMD), Al$_2$O$_3$ (J. T. Baker), and CBV 780 zeolite having a SiO$_2$/Al$_2$O$_3$ mole ratio of 80:1 (Zeolyst) were impregnated with silica tungstic acid hydrate as described above, except that the amount of silica tungstic acid hydrate was adjusted to provide 5, 10, or 20 weight percent loading of silica tungstic acid on the support, based on the total weight of support and silica tungstic acid. The impregnated supports were used as described below in Catalyst Preparation Method F to prepare catalysts comprising a first metal component, a second metal component, a heteropoly acid component, and a solid support.

Catalyst Preparation Method E

Preparation of Catalysts Comprising M1, M2, a Heteropoly Acid Component, and a Support A PtW/silica tungstic acid/TiO$_2$ catalyst containing 4 wt % Pt, a W/Pt weight ratio of 1, and 10 wt % silica tungstic acid was prepared as follows. 0.92 g of 10STA/TiO$_2$ (prepared as described herein above) that had been ground with a mortar and pestle and passed through a 400 microns mesh sieve was impregnated with 0.079 g of tetraammineplatinum (II) nitrate in 1.0 mL of water. The resulting slurry was mixed for 15 minutes, then dried overnight in a vacuum oven at 110° C. The resulting solid was allowed to cool to room temperature, and then wetted with 1.0 mL of water. To this was added 0.0532 g of ammonium tungsten oxide hydrate dissolved in 3.0 mL of water. The resulting mixture was stirred for 15 minutes. The material was then placed into a vacuum oven and dried overnight at 110° C. After cooling to room temperature, the material was transferred to a ceramic boat and calcined in air at 400° C. for three hours.

Additional catalysts containing a first metal component, a second metal component, a heteropoly acid, and a support were prepared using the general procedure detailed above, except with appropriate changes to the M1-containing salt, the M2-containing salt, the silica tungstic acid-impregnated support, and the amounts of the metal salts and of the impregnated support to prepare supported catalysts containing 4 wt % M1 and having a M2/M1 weight ratio of 1, wherein the supports comprised silica tungstic acid-impregnated SiO$_2$, silica tungstic acid-impregnated Al$_2$O$_3$, silica tungstic acid-impregnated CBV 780 zeolite, and the impregnated supports contained 5, 10, or 20 wt % silica tungstic acid.

Catalysts prepared according to Method E were used in Examples 61-72, and also in Examples 73-86. Results are presented in Tables 8 and 9.

Examples 61-70

Hydrodeoxygenation of 1,2,6-hexanetriol Using M1M2/Impregnated Support Catalysts Catalysts prepared according to Method E were used to hydrodeoxygenate 1,2,6-hexanetriol to a product mixture comprising 1,6-hexanediol according to the following procedure.

In each of Examples 61-70, approximately 1 g of an aqueous solution of 126HT (5 weight percent) and approximately 50 mg of the catalyst indicated in Table 8 were introduced with a stir bar into a 1.5 mL pressure vessel. The vessel was charged with H$_2$ to a pre-reduction pressure of about 145-150 psi, and then the pressure vessel was heated to 180° C. The contents were stirred for 1 hour before the pressure was raised to 1000 psig H$_2$; the pressure and temperature were maintained for 4 hours. The vessel was then cooled to Room temperature. The reaction mixture was filtered and the reaction solution analyzed using GC methods. Results are presented in Table 8.

TABLE 8

Results for Hydrodeoxygenation of 126HT Using Selected Catalysts Comprising a Heteropoly Acid-Impregnated Support and Prepared by Method E

| Ex | Catalyst | M1 | M1 wt % | M2 | M2/M1 molar ratio | Conv (%) | Sel 16HD (%) |
|----|------|------|------|------|------|------|------|
| 61 | PtRe/10STA/TiO$_2$ | Pt | 4 | Re | 1 | 78.02 | 51.0 |
| 62 | PtRe/10STA/CBV780 | Pt | 4 | Re | 1 | 68.44 | 40.3 |
| 63 | PtW/10STA/Al$_2$O$_3$ | Pt | 4 | W | 1 | 27.39 | 32.8 |
| 64 | PtW/10STA/TiO$_2$ | Pt | 4 | W | 1 | 89.07 | 76.4 |
| 65 | PtW/10STA/CBV780 | Pt | 4 | W | 1 | 77.92 | 72.6 |
| 66 | PtW/20STA/Al$_2$O$_3$ | Pt | 4 | W | 1 | 22.92 | 38.1 |
| 67 | PtW/20STA/SiO$_2$ | Pt | 4 | W | 1 | 86.96 | 65.4 |
| 68 | PtW/20STA/CBV780 | Pt | 4 | W | 1 | 90.63 | 48.9 |
| 69 | PtW/5STA/TiO$_2$ | Pt | 4 | W | 1 | 98.50 | 67.1 |
| 70 | PtW/5STA/CBV780 | Pt | 4 | W | 1 | 87.94 | 47.4 |

Examples 71-82

Hydrodeoxygenation of THPM Using M1M2/Impregnated Support Catalysts

Examples 71-82 were carried out following the procedure of Examples 61-70 except that 2-hydroxymethyltetrahydropyran (THPM) was used in place of 126HT and the catalysts were as indicated in Table 9. Conversion and selectivity to 16HD are included in Table 9.

TABLE 9

Results for Hydrodeoxygenation of THPM Using Selected Catalysts Prepared by Method E and Comprising a Heteropoly Acid-Impregnated Support

| Ex | Catalyst | M1 | M1 wt % | M2 | M2/M1 molar ratio | Conv (%) | Sel 16HD (%) |
|---|---|---|---|---|---|---|---|
| 71 | PtW/10STA/Al$_2$O$_3$ | Pt | 4 | W | 1 | 1.64 | 30.0 |
| 72 | PtW/10STA/SiO$_2$ | Pt | 4 | W | 1 | 30.77 | 83.9 |
| 73 | PtW/10STA/TiO$_2$ | Pt | 4 | W | 1 | 67.51 | 88.0 |
| 74 | PtW/10STA/CBV780 | Pt | 4 | W | 1 | 42.75 | 87.9 |
| 75 | PtW/20STA/Al$_2$O$_3$ | Pt | 4 | W | 1 | 1.27 | 30.4 |
| 76 | PtW/20STA/SiO$_2$ | Pt | 4 | W | 1 | 33.30 | 79.9 |
| 77 | PtW/20STA/TiO$_2$ | Pt | 4 | W | 1 | 34.34 | 84.9 |
| 78 | PtW/20STA/CBV780 | Pt | 4 | W | 1 | 39.48 | 84.0 |
| 79 | PtW/5STA/TiO$_2$ | Pt | 4 | W | 1 | 54.69 | 83.8 |
| 80 | PtW/5STA/CBV780 | Pt | 4 | W | 1 | 37.01 | 82.8 |
| 81 | PtRe/10STA/TiO$_2$ | Pt | 4 | Re | 1 | 73.08 | 88.3 |
| 82 | PtRe/10STA/CBV780 | Pt | 4 | Re | 1 | 18.01 | 76.5 |

Example 83

Unless otherwise specified, the reactions described in Examples 83-85 were carried out in a stainless steel (SS316) continuous trickle bed reactor (ID=0.4 cm) using the following procedure.

The reactor was packed with approximately 1 mL of catalyst. If the catalyst was not pre-reduced, the following procedure was used for in situ reduction: the reactor was heated at a rate of 1° C./min under forming gas (5% H$_2$ in N$_2$) to the desired reduction temperature, where it was held for the desired hold-up time, typically 2-3 hours. The pre-reduced or in-situ reduced catalyst was used for running multiple reactions under varying reaction conditions (temperature, pressure, feed concentrations). The reactor temperature was adjusted to the first target reaction condition temperature and held overnight under forming gas and either water or aqueous substrate solution. Subsequently the first reaction condition was started by changing the gas feed to 100% H$_2$ and the liquid feed to the desired aqueous substrate concentration. The liquid volumetric feed rate was adjusted to correspond to a target LHSV, which was measured in units of mL liquid feed/mL catalyst/h. Unless otherwise specified, the ratio of the gas volumetric flowrate to the liquid volumetric flowrate as measured at ambient conditions (GTO) was adjusted to a value of 4,000. Liquid effluent samples at each reaction condition were taken after continuous operation for a minimum of 24 hours. The liquid samples were analyzed by quantitative GC analysis.

Reactor feeds and reaction products were analyzed by gas chromatography using standard GC and GC/MS equipment: Agilent 5975C, HP5890, Stabilwax Column Restek Company Bellefonte, Pa. (30 m×0.25 mm, 0.5 micron film thickness). Chemical components of reaction product mixtures were identified by matching their retention times and mass spectra to those of authentic samples.

The catalyst used for Example 83, coprecipitated 4 wt % Pt/15 wt % Cs$_{2.5}$H$_{0.5}$PW$_{12}$O$_{40}$ on TiO$_2$, was prepared according to the following procedure.

The Cs salt of the tungsten heteropoly acid was prepared using an aqueous solution of Cs$_2$CO$_3$ and an aqueous solution of H$_3$PW$_{12}$O$_{40}$. The heteropoly acid H$_3$PW$_{12}$O$_{40}$ was prepared for use in aqueous solution by first dehydrating it at 65° C. under a vacuum for 10 hours. Cs$_2$CO$_3$ was dehydrated at 420° C. for 2 hours under a vacuum prior to its use for preparing an aqueous solution. Tetraammineplatinum (II) nitrate (Alfa Aesar) (2.396 g) was dissolved in 250 mL deionized water. To this solution, 24.48 g of TiO$_2$ solid support (<400 μm, Evonik Aerolyst 7708) was added followed by 16.99 mL of aqueous solution of H$_3$PW$_{12}$O$_{40}$ (0.08 mol/L), all while stirring. The above solution was titrated with an aqueous solution of 6.79 mL Cs$_2$CO$_3$ (0.25 mol/L) at room temperature at a rate of 1 mL/minute. The resulting white colloidal suspension was evaporated to a solid at 60° C. under vacuum on a rotary evaporator. After cooling to room temperature, the material was transferred to a ceramic boat and calcined in air at 350° C. for 4 hours.

For Example 83, the continuous reactor was charged with the catalyst prepared as described above. The catalyst was reduced in situ at 200° C. for 3 h. Solutions of 2.5 wt % 2-hydroxymethyltetrahydropyran or 2.5 wt % tetrahydrofuran dimethanol in 1,4-dioxane were used as the liquid feed. The liquid volumetric feed rate corresponded to a LHSV equal to 0.5 mL liquid feed/mL catalyst/h. Product yields are given in Table 10 for 120-180° C. under 100 bar H$_2$ pressure.

TABLE 10

Results for Example 83

| Feed | Temp (° C.) | 1H | 1P | THPM | 12HD | 15HD | 16HD | 15PD | c12CHD | THFdM | FdM | 126HT | Conv. (%) | Mole Balance (%) |
|---|---|---|---|---|---|---|---|---|---|---|---|---|---|---|
| THPM | 120 | 2 | <1 | 86 | <1 | <1 | 6 | <1 | <1 | <1 | <1 | <1 | 14 | 98 |
| THPM | 140 | 9 | <1 | 96 | <1 | <1 | 8 | <1 | <1 | <1 | <1 | <1 | 25 | 97 |
| THPM | 160 | 20 | 3 | 64 | <1 | <1 | 7 | <1 | <1 | <1 | <1 | <1 | 50 | 91 |
| THPM | 180 | 22 | 11 | 15 | <1 | <1 | 3 | <1 | <1 | <1 | <1 | <1 | 88 | 78 |
| THFdM | 120 | <1 | <1 | 2 | 1 | <1 | 1 | 1 | <1 | 120* | <1 | 9 | 13 | 108 |
| THFdM | 140 | 2 | <1 | 1 | 7 | 4 | 5 | 1 | <1 | 78 | <1 | 21 | 45 | 100 |

*Yield high due to high mass balance

Example 84

The catalyst used for Example 84, impregnated 4 wt % Pt/15 wt % $Cs_{2.5}H_{0.5}PW_{12}O_{40}$ on $TiO_2$, was prepared according to the following procedure.

The Cs salt of the tungsten heteropoly acid was prepared using an aqueous solution of $Cs_2CO_3$ and an aqueous solution of $H_3PW_{12}O_{40}$. The heteropoly acid $H_3PW_{12}O_{40}$ was prepared for use in aqueous solution by first dehydrating it at 65° C. under a vacuum for 10 hours. $Cs_2CO_3$ was dehydrated at 420° C. for 2 hours under a vacuum prior to its use for preparing an aqueous solution. Cs-exchanged heteropoly acids on $TiO_2$ were prepared by titrating aqueous solution 106.67 mL of $H_3PW_{12}O_{40}$ (0.08 mol/L) with 153.0 g of $TiO_2$ (<400 μm, Evonik Aerolyst 7708) and 400 mL deionized water while stirring, with 42.47 mL of an aqueous solution of $Cs_2CO_3$ (0.25 mol/L) at room temperature at a rate of 1 mL/minute. The resulting white colloidal suspension was evaporated to a solid at 60° C. under a vacuum on a rotary evaporator, ground with a mortar and pestle and passed through a 400 microns sieve. The dried solids were calcined in air at 300° C. for 4 hour.

20.0 g of $Cs_{2.5}H_{0.5}PW_{12}O_{40}/TiO_2$ was impregnated with 1.664 g of tetraammineplatinum (II) nitrate (Alfa Aesar) dissolved in 13.45 mL of water, then dried overnight in a drying oven at 80° C. After cooling to room temperature, the material was transferred to a ceramic boat and calcined in air at 350° C. for 4 hours.

For Example 84, the continuous reactor was charged with the catalyst prepared as described above. The catalyst was reduced in situ at 200° C. for 3 h. Solutions of 2.5 wt % 2-hydroxymethyltetrahydropyran or 2.5 wt % tetrahydrofuran dimethanol in 1,4-dioxane were used as the liquid feed. The liquid volumetric feed rate corresponded to a LHSV equal to 0.5 mL liquid feed/mL catalyst/h. Product yields are given in Table 11 for 120-180° C. under 100 bar $H_2$ pressure.

Example 85

The catalyst used for Example 85, impregnated 20 wt % Ni/15 wt % $Cs_{2.5}H_{0.5}PW_{12}O_{40}$ on $TiO_2$, was prepared according to the following procedure.

The Cs salt of the tungsten heteropoly acid was prepared using an aqueous solution of $Cs_2CO_3$ and an aqueous solution of $H_3PW_{12}O_{40}$. The heteropoly acid $H_3PW_{12}O_{40}$ was prepared for use in aqueous solution by first dehydrating it at 65° C. under a vacuum for 10 hours. $Cs_2CO_3$ was dehydrated at 420° C. for 2 hours under a vacuum prior to its use for preparing an aqueous solution. Cs-exchanged heteropolyacids on $TiO_2$ were prepared by titrating aqueous solution 106.67 mL of $H_3PW_{12}O_{40}$ (0.08 mol/L) with 153.0 g of $TiO_2$ (<400 μm, Evonik Aerolyst 7708) and 400 mL deionized water, with 42.47 mL of an aqueous solution of $Cs_2CO_3$ (0.25 mol/L) at room temperature at a rate of 1 mL/minute. The resulting white colloidal suspension was evaporated to a solid at 60° C. under a vacuum on a rotary evaporator, ground with a mortar and pestle and passed through a 400 microns sieve. The dried solids were calcined in air at 300° C. for 4 hour.

20.0 g of $Cs_{2.5}H_{0.5}PW_{12}O_{40}/TiO_2$ was impregnated with 20.038 g of Nickel (II) (Alfa Aesar) nitrate hexahydrate dissolved in 5.65 mL of water, then dried overnight in a drying oven at 80° C. After cooling to room temperature, the material was transferred to a ceramic boat and calcined in air at 350° C. for 4 hours.

For Example 85, the continuous reactor was charged with the catalyst prepared as described above. The catalyst was reduced in situ at 250° C. for 3 h. Solutions of 2.5 wt % 2-hydroxymethyltetrahydropyran or 2.5 wt % tetrahydrofuran dimethanol in 1,4-dioxane were used as the liquid feed. The liquid volumetric feed rate corresponded to a LHSV equal to 0.5 mL liquid feed/mL catalyst/h. Product yields are given in Table 12 for 200-260° C. under 100 bar $H_2$ pressure.

TABLE 11

Results for Example 84

| Feed | Temp. (° C.) | Product Molar Yields (mole %) | | | | | | | | | | Conv. (%) | Mole Balance (%) |
|---|---|---|---|---|---|---|---|---|---|---|---|---|---|---|
| | | 1H | 1P | THPM | 12HD | 15HD | 16HD | 15PD | c12CHD | THFdM | FdM | 126HT | | |
| THPM | 120 | 8 | <1 | 76 | <1 | <1 | 8 | <1 | <1 | <1 | <1 | <1 | 24 | 97 |
| THPM | 140 | 30 | 3 | 51 | <1 | <1 | 10 | <1 | <1 | <1 | <1 | <1 | 60 | 91 |
| THPM | 160 | 27 | 9 | 15 | <1 | <1 | 4 | <1 | <1 | <1 | <1 | <1 | 88 | 66 |
| THPM | 180 | 9 | 15 | 2 | <1 | <1 | 1 | <1 | <1 | <1 | <1 | <1 | 98 | 66 |
| THFdM | 120 | <1 | <1 | 2 | 1 | <1 | 1 | <1 | <1 | 127* | <1 | 7 | 8 | 109 |
| THFdM | 140 | 1 | <1 | 1 | 4 | 1 | 3 | 1 | <1 | 100* | <1 | 18 | 29 | 103 |

*Yield high due to high mass balance

TABLE 12

Results for Example 85

| Feed | Temp. (°C.) | 1H | 1P | THPM | 12HD | 15HD | 16HD | 15PD | c12CHD | THFdM | FdM | 126HT | Conv. (%) | Mole Balance (%) |
|---|---|---|---|---|---|---|---|---|---|---|---|---|---|---|
| THPM | 200 | 2 | <1 | 88 | <1 | <1 | <1 | <1 | <1 | <1 | <1 | <1 | 12 | 97 |
| THPM | 260 | 13 | 9 | 2 | <1 | <1 | <1 | <1 | <1 | 4 | <1 | 3 | 99 | 74 |
| THFdM | 200 | 8 | 2 | 12 | 4 | <1 | 2 | <1 | <1 | 80 | 1 | <1 | 44 | 95 |
| THFdM | 220 | 25 | 6 | 26 | <1 | <1 | 3 | <1 | <1 | 2 | <1 | <1 | 98 | 73 |

What is claimed is:

1. A process for preparing an α,ω-$C_n$-diol, comprising the steps:
    (a) providing a feedstock comprising a $C_n$ oxygenate;
    (b) contacting the feedstock with hydrogen gas, in the presence of a catalyst and at a temperature and for a time sufficient to form a product mixture comprising an α,ω-$C_n$-diol;
    wherein n is 5 or greater; and wherein the catalyst comprises a first metal component, a heteropoly acid component, optionally a second metal component, optionally at least one promoter, and optionally a support; wherein:
    the first metal component comprises Ni, Ir, Pt, Rh, Ru, Pd, Fe, Ag, or Au;
    the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof;
    the second metal component comprises Cr, a Cr oxide, Ni, a Ni oxide, Fe, a Fe oxide, Co, a Co oxide, Mn, a Mn oxide, Mo, a Mo oxide, W, a W oxide, Re, a Re oxide, Zn, a Zn oxide, $SiO_2$, or $Al_2O_3$; and
    the promoter comprises Na, K, Mg, Rb, Cs, Ca, Sr, Ba, Ce, or mixtures thereof.

2. The process of claim 1 wherein n=5 or 6.

3. The process of claim 1, wherein the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof.

4. The process of claim 3, wherein the support comprises $SiO_2$, $TiO_2$, zeolites, or mixtures thereof.

5. The process of claim 1, wherein the $C_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxy-hexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural with ketones and/or aldehydes; and condensation products from the reaction of furfural with ketones and/or aldehydes.

6. The process of claim 5, wherein the $C_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof.

7. The process of claim 6, wherein the $C_n$ oxygenate comprises 1,2,6-hexanetriol.

8. The process of claim 5, wherein the $C_n$ oxygenate comprises 1,2,5-pentanetriol; furfural; furfuryl alcohol; tetrahydrofurfuryl alcohol; xylitol; or mixtures thereof.

9. The process of claim 1, wherein the first metal component comprises Ni, Pt, Pd, Fe, or Ru.

10. The process of claim 1, wherein the heteropoly acid component comprises $H_3[P(W_3O_{10})_4]$, $H_4[Si(W_3O_{10})_4]$, or $Cs_{2.5}H_{0.5}[P(W_3O_{10})_4]$.

11. The process of claim 1, wherein the optional second metal component is present in the catalyst and comprises W or Re.

12. The process of claim 1, wherein the optional promoter is present in the catalyst and comprises Cs.

13. The process of claim 1, wherein the first metal component comprises Ni, Pt, Pd, Fe, or Ru; the heteropoly acid component comprises $H_3[P(W_3O_{10})_4]$, $H_4[Si(W_3O_{10})_4]$, or $Cs_{2.5}H_{0.5}[P(W_3O_{10})_4]$; and the optional second metal component is present in the catalyst and comprises W or Re.

14. The process of claim 1, further comprising the steps:
    (c) optionally, isolating the α,ω-$C_n$-diol from the product mixture;
    (d) contacting the α,ω-$C_n$-diol with ammonia and hydrogen in the presence of a reductive amination catalyst at a temperature and for a time sufficient to form a second product mixture comprising an α,ω-$C_n$-diaminoalkane; and
    (e) optionally, isolating the α,ω-$C_n$-diaminoalkane from the second product mixture.

15. The process of claim 14, wherein the α,ω-$C_n$-diaminoalkane comprises 1,6-diaminohexane.

* * * * *